(12) United States Patent
Nagasaka

(10) Patent No.: US 9,939,456 B2
(45) Date of Patent: Apr. 10, 2018

(54) EXERCISE SUPPORT DEVICE, CONTROL METHOD FOR EXERCISE SUPPORT DEVICE, AND COMPUTER-READABLE STORAGE MEDIUM

(71) Applicant: CASIO COMPUTER CO., LTD., Tokyo (JP)

(72) Inventor: Tomoaki Nagasaka, Koganei (JP)

(73) Assignee: CASIO COMPUTER CO., LTD., Tokyo (JP)

( * ) Notice: Subject to any disclaimer, the term of this patent is extended or adjusted under 35 U.S.C. 154(b) by 637 days.

(21) Appl. No.: 14/489,302

(22) Filed: Sep. 17, 2014

(65) Prior Publication Data

US 2015/0081245 A1    Mar. 19, 2015

(30) Foreign Application Priority Data

Sep. 19, 2013   (JP) ................. 2013-193729

(51) Int. Cl.
| | |
|---|---|
| *A63B 24/00* | (2006.01) |
| *G01P 15/04* | (2006.01) |
| *G01P 3/02* | (2006.01) |
| *G01P 15/18* | (2013.01) |
| *G01P 3/64* | (2006.01) |
| *G06F 19/00* | (2018.01) |

(Continued)

(52) U.S. Cl.
CPC .............. *G01P 3/64* (2013.01); *A61B 5/1126* (2013.01); *G06F 19/3481* (2013.01); *G06K 9/00342* (2013.01); *A61B 2562/0219* (2013.01)

(58) Field of Classification Search
CPC .......... A61B 2562/0219; A61B 5/1126; A61B 5/1071; A61B 5/1122; A61B 5/6824; A61B 5/6828; A61B 5/6898; G01P 3/64; G01P 13/00; G06F 19/3481; G06K 9/00342; G06Q 10/0639
USPC ................ 702/141, 175, 176, 150; 348/169; 382/154, 173; 434/247
See application file for complete search history.

(56) References Cited

U.S. PATENT DOCUMENTS

| | | | |
|---|---|---|---|
| 6,018,705 A | 1/2000 | Gaudet et al. | |
| 6,052,654 A | 4/2000 | Gaudet et al. | |
| 8,460,001 B1* | 6/2013 | Chuang | .............. G09B 19/0038 434/247 |

FOREIGN PATENT DOCUMENTS

JP        2009-160392        7/2009

* cited by examiner

*Primary Examiner* — John H Le
(74) *Attorney, Agent, or Firm* — Fitch Even Tabin & Flannery LLP

(57) ABSTRACT

In an exercise support device of the present invention, acceleration signals in three axis directions including vertical, longitudinal, and lateral directions corresponding to the motion of a user performing exercise of cyclically moving feet are obtained, and a first maximum value in one cycle of a foot movement in the vertical acceleration signal is obtained. Subsequently, a search is made for first and second change points related to foot landing and takeoff motions in a composite acceleration signal obtained by combining acceleration signals in at least two axis directions, in forward and backward directions of the time point of a second maximum value of the composite acceleration signal, within the cycle. Then, a time period between the first and second change points is obtained as a change point interval, and a foot landing period while exercising is calculated based on the first maximum value and the change point interval.

17 Claims, 23 Drawing Sheets

(51) Int. Cl.
*G06K 9/00* (2006.01)
*A61B 5/11* (2006.01)

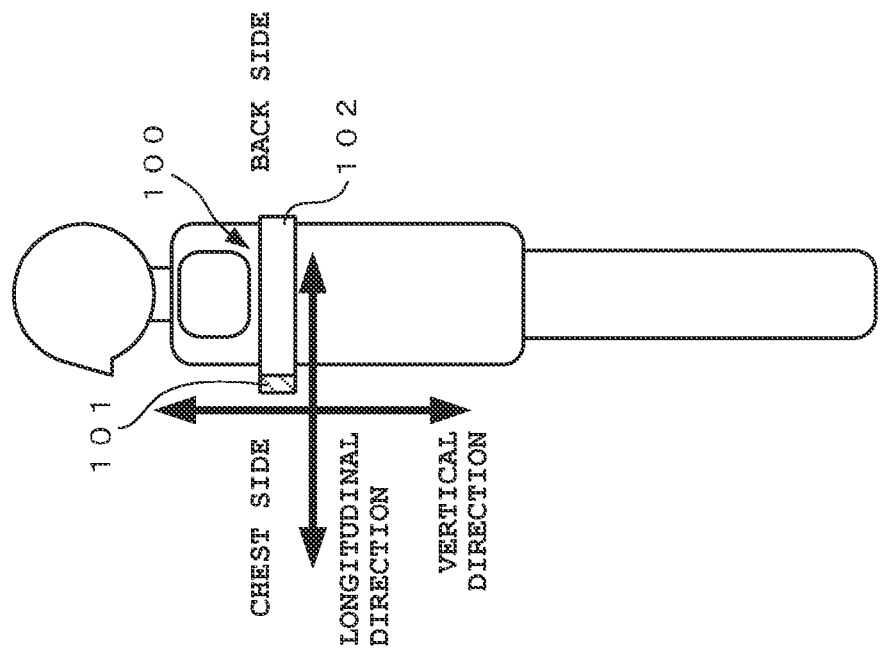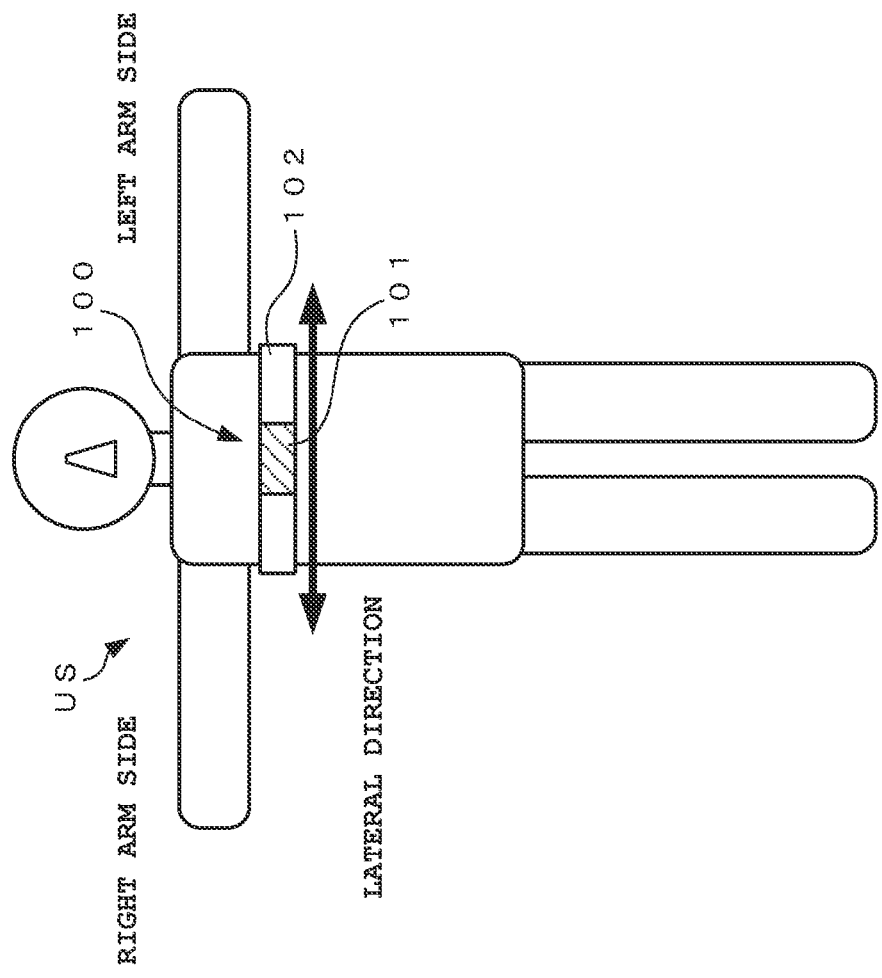

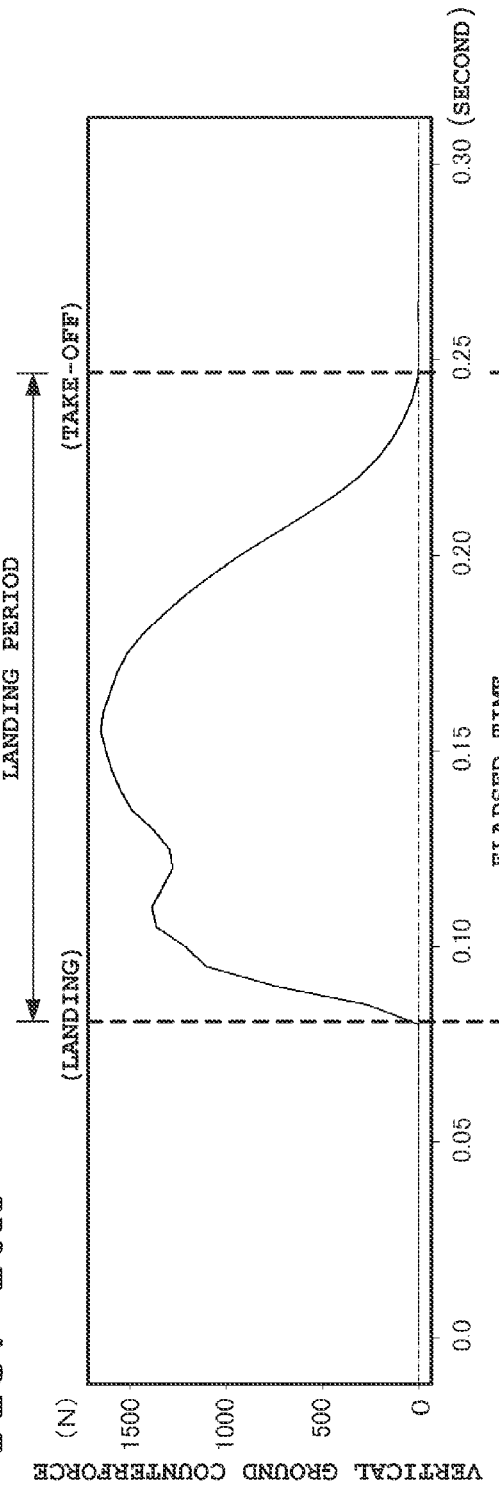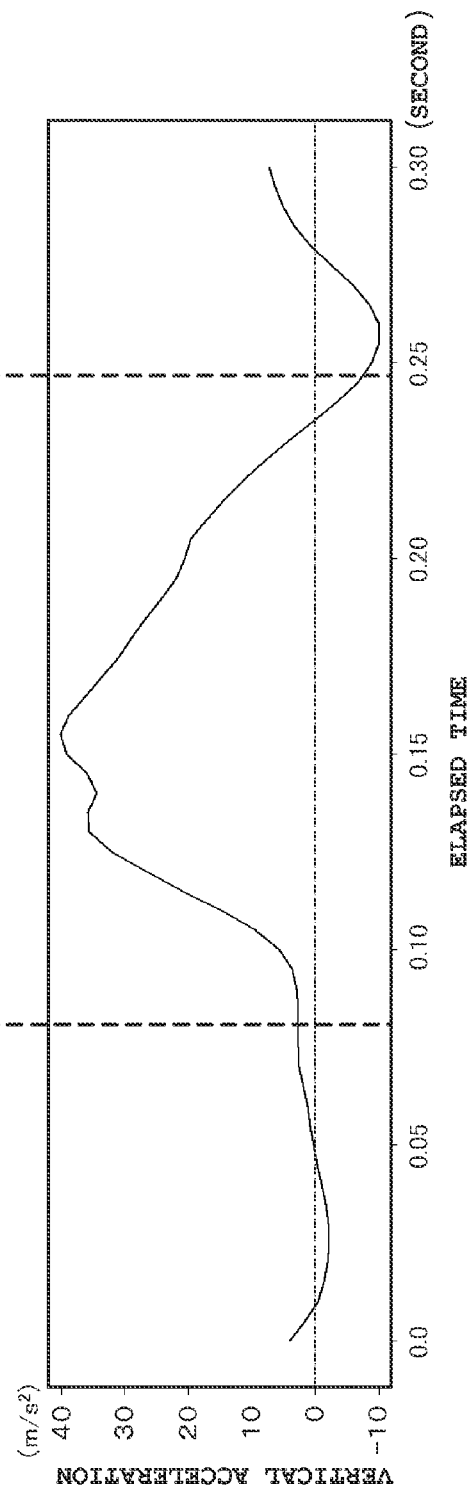

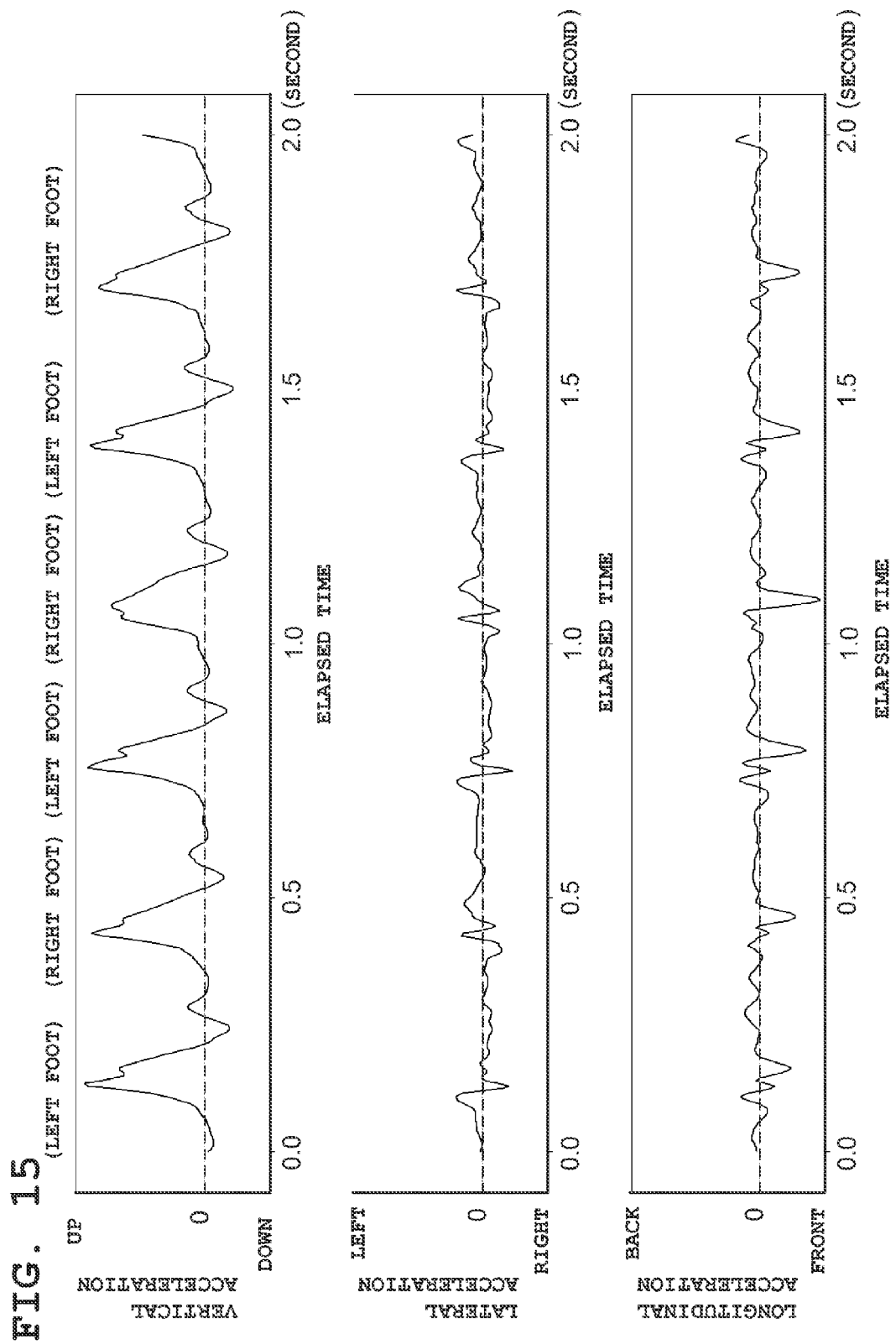

FIG. 16A
FIG. 16B
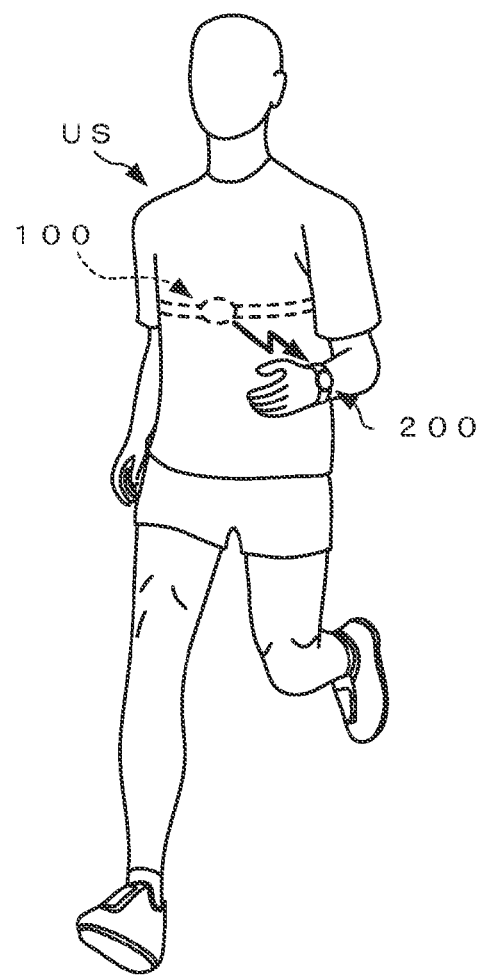
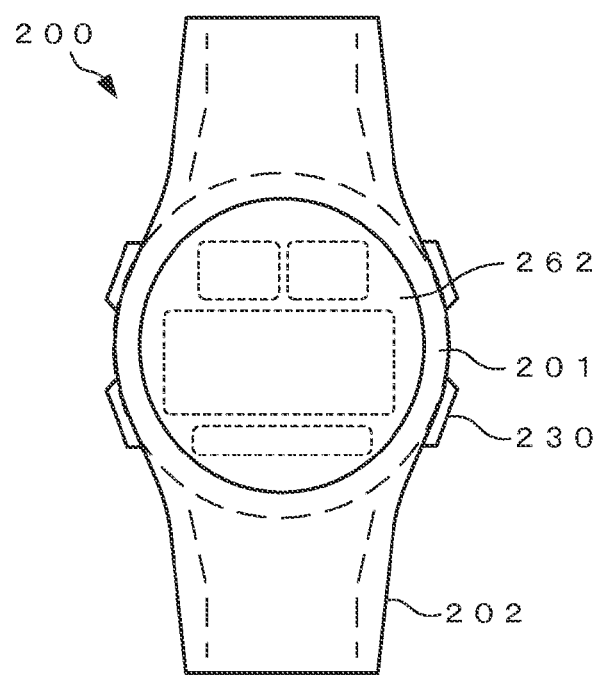

EXERCISE SUPPORT DEVICE, CONTROL METHOD FOR EXERCISE SUPPORT DEVICE, AND COMPUTER-READABLE STORAGE MEDIUM

CROSS-REFERENCE TO RELATED APPLICATION

This application is based upon and claims the benefit of priority from the prior Japanese Patent Application No. 2013-193729, filed Sep. 19, 2013, the entire contents of which are incorporated herein by reference.

BACKGROUND OF THE INVENTION

1. Field of the Invention

The present invention relates to an exercise support device, an exercise support method, and an exercise support program. Specifically, the present invention relates to an exercise support device, an exercise support method, and an exercise support program by which the motion status (exercise status) of a human body at the time of exercise can be precisely grasped to be determined and improved.

2. Description of the Related Art

In recent years, because of rising health consciousness and rising interest in participation in races, more and more people are performing daily exercises, such as running, walking, and cycling, to maintain their wellness, improve their health condition, or participate in races.

These people are very conscious of and interested in measuring various biological information and exercise information and recording the measurement results in order to grasp their own health conditions and exercise status and achieve efficient and effective training.

As an item to be measured for the above-described purposes, a foot landing period and a foot lifting period while exercising (while running) have been conventionally known.

Here, the foot landing period can serve as, for example, a guideline for estimating the fatigued state of a human body or a guideline for recognizing whether the way of running such as "pitch running" or "stride running" is being appropriately performed. Also, it is possible to calculate a gait, a moving speed, a travelling distance, an energy consumption amount, and the like based on this foot landing period.

As a method for calculating a foot landing period while exercising, various methods have been proposed. In one of these methods, a force plate, which is a mechanical measurement device, is stepped while running, and a foot landing period is calculated from a period of time in which force is exerted. In another method, a foot landing period is calculated from moving images captured by a high-speed camera. In still another method, a foot landing period is estimated by a motion sensor being worn on a foot.

For example, the average value of foot landing periods can also be calculated by positive and negative spikes representing an instant when a foot of the user lands on the ground and an instant when the foot of the user takes off from the ground being detected based on a signal waveform obtained by an accelerometer while exercising and a time interval between these spikes being measured, as described in Japanese Patent Application Laid-Open (Kokai) Publication No. 2009-160392.

Among the various methods for calculating a foot landing period, a foot landing period can be relatively accurately calculated in the method using a force plate and the method using a high-speed camera. However, devices for these methods are bulky and expensive. Therefore, they are available only in part of educational or gymnastic organizations, and cannot be used by ordinary people. Also, these devices can obtain data of only several footsteps within a narrow range where the force plate is installed or the range of the imaging field of the high-speed camera.

On the other hand, the method where a motion sensor is worn on a foot is advantageous in that information regarding lower limbs can be exclusively obtained. However, other information such as the motion status of the upper body and a heart rate while exercising cannot be simultaneously obtained. Accordingly, when these pieces of information are to be acquired, a sensor or the like has to be further worn on a different body part.

Also, according to verification by the inventor, in the calculation method of the above-described technique based on acceleration data, foot landing timing and takeoff timing cannot be precisely detected and therefore foot landing periods cannot be accurately calculated. This verification result will be specifically described in embodiments described further below.

SUMMARY OF THE INVENTION

The present invention is to provide an exercise support device, an exercise support method, and an exercise support program by which a foot landing period while exercising is precisely estimated and the user is provided with support information that can be used to grasp, judge, and improve the user's own exercise status, with a simple structure.

In accordance with one aspect of the present invention, there is provided an exercise support device comprising: an acceleration measuring section which obtains acceleration signals in three axis directions including a vertical direction, a longitudinal direction, and a lateral direction corresponding to a motion of a body of a user performing exercise of cyclically moving feet; a vertical acceleration maximum value obtaining section which obtains a first maximum value within a period of one cycle of a foot movement of the user in an acceleration signal in the vertical direction obtained by the acceleration measuring section; a signal processing section which searches for a first change point related to foot landing and takeoff motions of the user in a composite acceleration signal obtained by combining acceleration signals in at least two of the three axis directions, in a forward direction of a time point of a second maximum value of the composite acceleration signal, and a second change point related to foot landing and takeoff motions of the user in the composite acceleration signal, in a backward direction of the time point of the second maximum value, within the period of one cycle; and a landing period calculating section which obtains a period of time between the first change point and the second change point as a change point interval, when the first change point and the second change point are detected by search in the signal processing section, and calculates a foot landing period of the user during the exercise based on the first maximum value of the acceleration signal in the vertical direction and the change point interval.

In accordance with another aspect of the present invention, there is provided an exercise support method comprising: a step of obtaining acceleration signals in three axis directions including a vertical direction, a longitudinal direction, and a lateral direction corresponding to a motion of a body of a user performing exercise of cyclically moving feet; a step of obtaining a first maximum value within a period of one cycle of a foot movement of the user in an acceleration signal in the vertical direction; a step of searching for a first change point related to foot landing and takeoff motions of the user in a composite acceleration signal obtained by combining acceleration signals in at least two of the three axis directions, in a forward direction of a time point of a second maximum value of the composite acceleration signal, and a second change point related to foot landing and takeoff motions of the user in the composite acceleration signal, in a backward direction of the time point of the second maximum value, within the period of one cycle; and a step of obtaining a period of time between the first change point and the second change point as a change point interval, when the first change point and the second change point are detected in the step of searching for the first change point and the second change point, and calculating a foot landing period of the user during the exercise based on the first maximum value of the acceleration signal in the vertical direction and the change point interval.

In accordance with another aspect of the present invention, there is provided a non-transitory computer-readable medium having stored thereon an exercise support program that is executable by a computer, the program being executable by the computer to perform functions comprising: processing for obtaining acceleration signals in three axis directions including a vertical direction, a longitudinal direction, and a lateral direction corresponding to a motion of a body of a user performing exercise of cyclically moving feet; processing for obtaining a first maximum value within a period of one cycle of a foot movement of the user in an acceleration signal in the vertical direction processing for searching for a first change point related to foot landing and takeoff motions of the user in a composite acceleration signal obtained by combining acceleration signals in at least two of the three axis directions, in a forward direction of a time point of a second maximum value of the composite acceleration signal, and a second change point related to foot landing and takeoff motions of the user in the composite acceleration signal, in a backward direction of the time point of the second maximum value, within the period of one cycle; and processing for obtaining a period of time between the first change point and the second change point as a change point interval, when the first change point and the second change point are detected in the processing for searching for the first change point and the second change point, and calculating a foot landing period of the user during the exercise based on the first maximum value of the acceleration signal in the vertical direction and the change point interval.

The above and further objects and novel features of the present invention will more fully appear from the following detailed description when the same is read in conjunction with the accompanying drawings. It is to be expressly understood, however, that the drawings are for the purpose of illustration only and are not intended as a definition of the limits of the invention.

BRIEF DESCRIPTION OF THE DRAWINGS

FIG. 1A and FIG. 1B are schematic diagrams showing an example where an exercise support device according to a first embodiment of the present invention has been worn on a human body;

FIG. 10A and FIG. 10B are diagrams showing a relation between a foot landing period (actual foot landing period) found based on ground reaction force and vertical acceleration;

FIG. 15 is a signal waveform diagram of an example of acceleration signals in three axis directions corrected by the processing for correcting the axes of acceleration signals according to the second embodiment;

FIG. 16A and FIG. 16B are schematic diagrams of an exercise support device according to a third embodiment of the present invention;

DETAILED DESCRIPTION OF THE PREFERRED EMBODIMENTS

Figure 2:
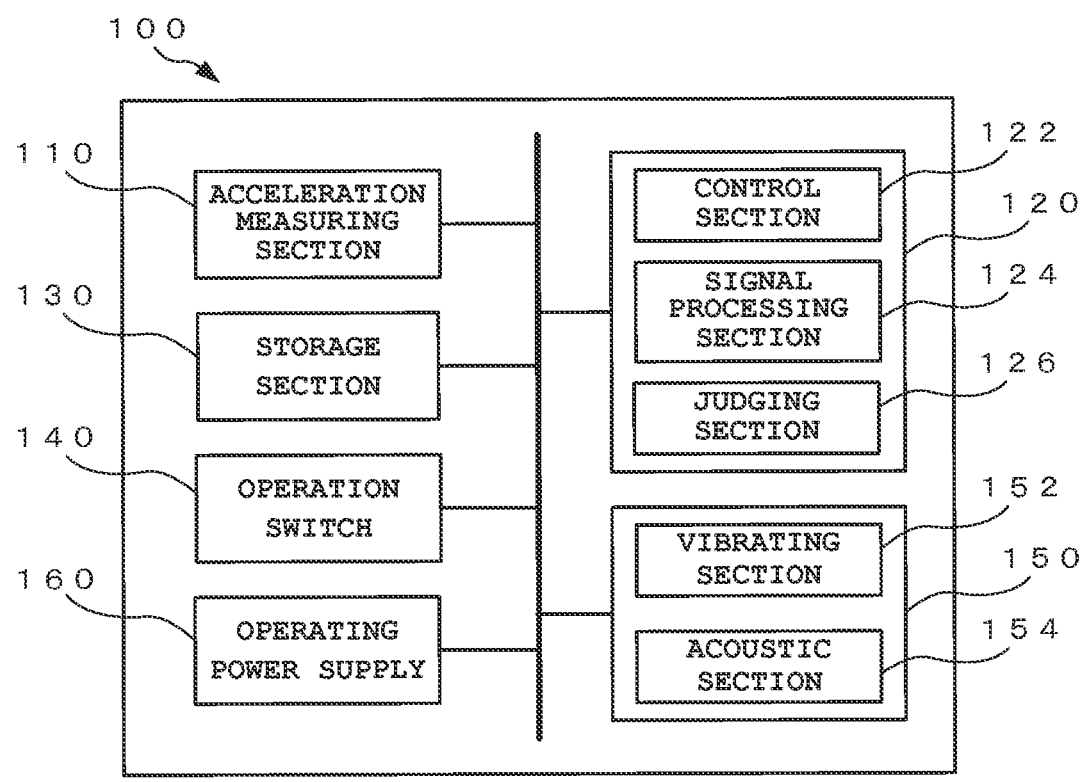
FIG. 2 is a functional block diagram showing a structural example of the exercise support device according to the first embodiment.

Hereafter, an exercise support device, an exercise support method, and an exercise support program according to the present invention are described in detail with reference to the drawings.

Note that, although embodiments described below are provided with various technically-preferable limitations in order to carry out the present invention, these limitations are not intended to limit the scope of the present invention to the embodiments and examples shown in the drawings.

<First Embodiment>
(Exercise Support Device)

FIG. 1A and FIG. 1B are schematic diagrams showing an example where an exercise support device according to a first embodiment of the present invention has been worn on a human body.

Here, FIG. 1A is a schematic diagram of a state where the exercise support device according to the present embodiment has been worn on the human body, when viewed from a front (chest) side.

FIG. 1B is a schematic diagram of a state where the exercise support device according to the present embodiment has been worn on the human body, when viewed from a left arm side.

FIG. 2 is a functional block diagram showing a structural example of the exercise support device according to the present embodiment.

Here, for convenience of explanation, exchanges of signals and data among functional blocks are depicted to be simultaneously performed. However, in practice, exchanges of signals and data are performed as needed based on an exercise support method described below.

The exercise support device according to the first embodiment includes, for example, a chest-mount-type sensor device (hereinafter referred to as a "chest device" for convenience of explanation) which is worn on the chest of a user US who is a measurement subject, as shown in FIG. 1A and FIG. 1B.

The chest device 100 mainly includes, for example, a device body 101 that detects the exercise status and biological information of the user US and provides predetermined exercise support information, and a belt section 102 that is wound around the chest of the user US so that the device body 101 is worn on the user US, as shown in FIG. 1A and FIG. 1B.

Specifically, the chest device 100 (device body 101) mainly includes, for example, an acceleration measuring section 110, a computation processing circuit 120, a storage section 130, an operation switch 140, a notifying section 150, and an operating power supply 160, as shown in FIG. 2.

The acceleration measuring section 110 measures the ratio of change in motion speed while the user is exercising (running exercise).

In the present embodiment, the acceleration measuring section 110, which has a triaxial acceleration sensor, detects acceleration components in three axis directions orthogonal to one another, and outputs the detection results as acceleration signals (acceleration data).

This acceleration measuring section 110 detects acceleration components in a vertical direction (gravity direction), a longitudinal direction (forward and backward direction at the time of exercise), and a lateral direction (an extending direction of left and right arms in the drawings), as shown in FIG. 1A and FIG. 1B.

The acceleration signals in the respective directions obtained by the acceleration measuring section 110 are associated with time data generated in the computation processing circuit 120, stored in a predetermined storage area of the storage section 130, and used in processing for estimating a foot landing period in the computation processing circuit 120 (signal processing section 124).

The computation processing circuit 120 is a computation processing device, such as a CPU (Central Processing Unit) or MPU (Micro Processing Unit) having a timing function, and includes a control section 122, a signal processing section (a vertical acceleration maximum value obtaining section, an extreme value interval obtaining section, and a landing period calculating section) 124, and a judging section 126.

The control section 122 performs processing in accordance with a predetermined control program based on a predetermined operation clock, and thereby controls operations in the respective sections in the device body 101, such as a sensing operation in the acceleration measuring section 110, operations for storing and reading various data in and from the storage section 130, and a notifying operation in the notifying section 150, so as to achieve a predetermined function.

The signal processing section 124 performs processing in accordance with a predetermined algorithm program based on a predetermined operation clock, and thereby obtains, for each cycle (one footstep) in cyclic motions of feet while exercising, a maximum value (P) of an acceleration signal in the vertical direction and an interval between change points (change point interval, extreme value interval: W) related to foot landing and takeoff in composite acceleration signals in the vertical direction and the longitudinal direction.

Based on these feature amounts, the signal processing section 124 calculates (estimates) a foot landing period by using a predetermined formula. The foot landing period calculated by the signal processing section 124 is stored in a predetermined storage area of the storage section 130.

The judging section 126 performs analysis processing for comparing a foot landing period calculated by the signal processing section 124 with, for example, a numerical value range set in advance.

For example, based on a calculated foot landing period, the judging section 126 obtains various exercise information related to the foot landing period (for example, a fatigued state, the way of running, a moving speed, and an energy consumption amount) and judges the appropriateness of the exercise information.

Then, based on these judgment results, the judging section 126 outputs a notification signal for controlling the operation of the notifying section 150, and stores the judgment results in a predetermined storage area of the storage section 130.

The storage section 130 has a non-volatile memory, and stores an acceleration signal obtained by the acceleration measuring section 110 in a predetermined storage area in association with time data.

This storage section 130 temporarily stores various data that are used when processing is performed in the above-described computation processing circuit 120 in accordance with a predetermined control program or algorithm program, or generated when processing is performed in accordance with the program.

In addition, the storage section 130 stores, in a predetermined storage area, a foot landing period obtained by the above-described signal processing section 124 performing processing in accordance with the predetermined algorithm program, various exercise information related to the foot landing period, and results of the judgment of the exercise information.

Here, the storage section 130 may include a ROM (Read Only Memory) or a flash memory to store the control program or algorithm program to be executed in the above-described computation processing circuit 120.

Note that a non-volatile memory portion constituting the storage section 130 may be partially or entirely in a form of a removable storage medium such as a memory card, and may be structured to be removable from the chest device 100.

The operation switch 140 includes at least a power supply switch. By the user US operating the operation switch 140, driving electric power to be supplied from the operating power supply 160 to each section in the device body 101 is supplied or interrupted to control ON (start) and OFF (stop) of the power supply of the chest device.

Note that a structure may be adopted in which the operation switch 140 includes a sensor control switch and the start or end of a sensing operation in the acceleration measuring section 110 is controlled by the user US operating the operation switch 140.

Also note that a structure may be adopted in which the operation switch 140 includes only the power supply switch, and a sensing operation in the acceleration measuring section 110 is started by the user US operating the operation switch 140 to turn the power supply of the device body 101 ON (start the power supply), and ended by the power supply of the device body 101 being turned OFF (stopping the power supply).

The notifying section (information providing section) 150 has, for example, a vibrating section 152 and an acoustic section 154, and generates predetermined vibration information and sound information based on a notification signal from the computation processing circuit 120 (judging section 126) so as to notify the user US of exercise support information.

The vibrating section 152 has a vibrating device (vibrator) such as a vibration motor or oscillator and, by generating vibration information such as a predetermined vibration pattern or its magnitude, tactually provides or reports various information to the user US.

The acoustic section 154 has an acoustic device such as a buzzer or loudspeaker. By generating sound information such as a predetermined timbre, a sound pattern, or a voice message, the acoustic section 154 aurally provides or reports various information to the user US.

Note that the notifying section 150 may include both of the vibrating section 152 and the acoustic section 154, or may include only one of them.

The operating power supply 160 supplies driving electric power to each section of the chest device 100 (device body 101). As the operating power supply 160, for example, a primary battery such as a commercially-available coin-shaped battery or button-shaped battery or a secondary battery such as a lithium-ion battery or a nickel-metal-hydride battery can be used.

In addition to these primary battery and secondary battery, it is possible to apply a power supply by an energy harvest technology for generating electricity by energy such as vibrations, light, heat, and electro-magnetic waves, as the operating power supply 160.

(Exercise Support Method)

Next, an exercise support method for the exercise support device according to the present embodiment is described.

Figure 3:
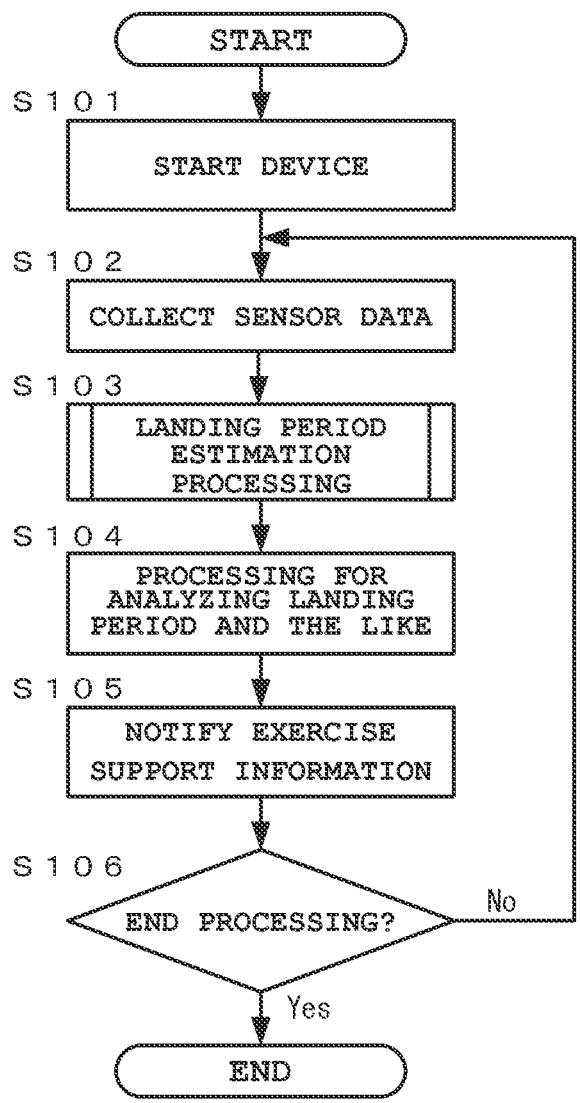
FIG. 3 is a flowchart of an example of an exercise support method to be performed for the exercise support device according to the first embodiment.

FIG. 3 is a flowchart of an example of the exercise support method to be performed for the exercise support device according to the present embodiment.

Figure 4:
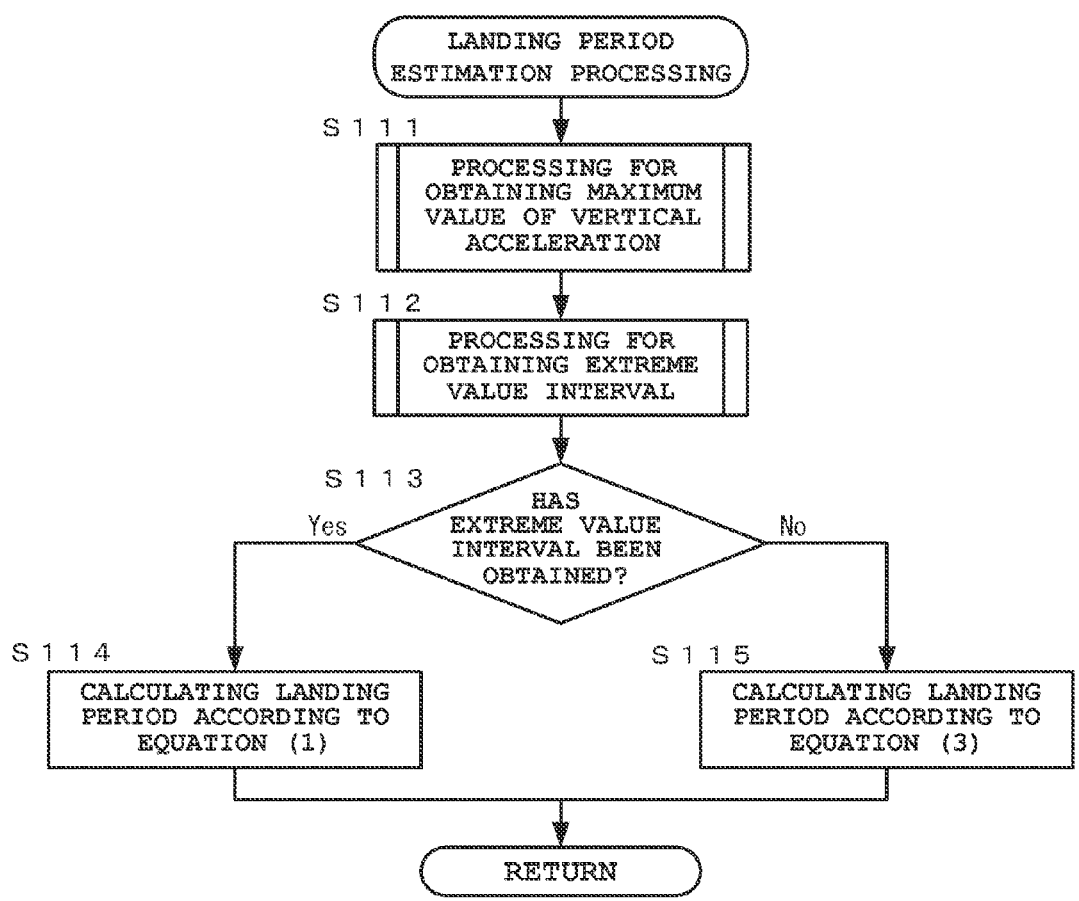
FIG. 4 is a flowchart of an example of a method for estimating a foot landing period, which is applied to the exercise support method according to the first embodiment.

FIG. 4 is a flowchart of an example of a method for estimating a foot landing period, which is applied to the exercise support method according to the present embodiment.

Figure 5:
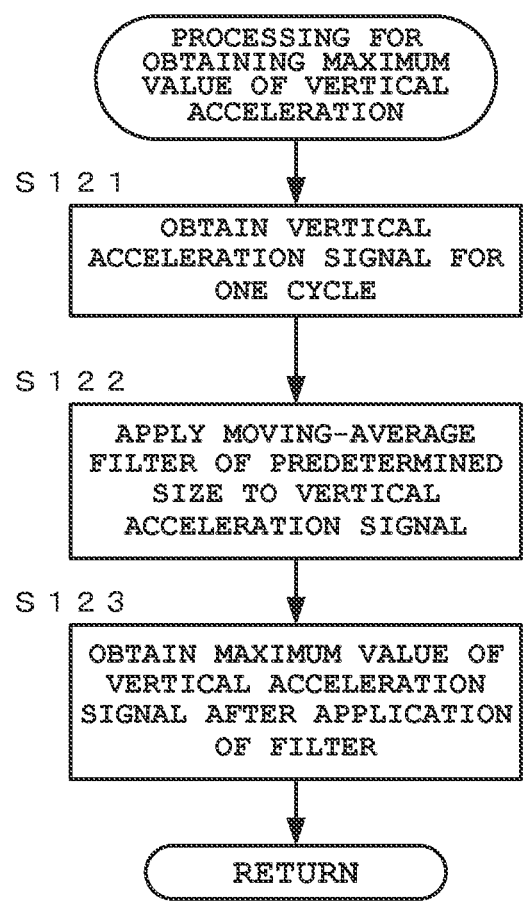
FIG. 5 is a flowchart of an example of processing for obtaining the maximum value of an acceleration signal in a vertical direction, which is applied to the landing period estimation method according to the first embodiment.

FIG. 5 is a flowchart of an example of processing for obtaining the maximum value of an acceleration signal in a vertical direction, which is applied to the landing period estimation method according to the present embodiment.

Figure 6:
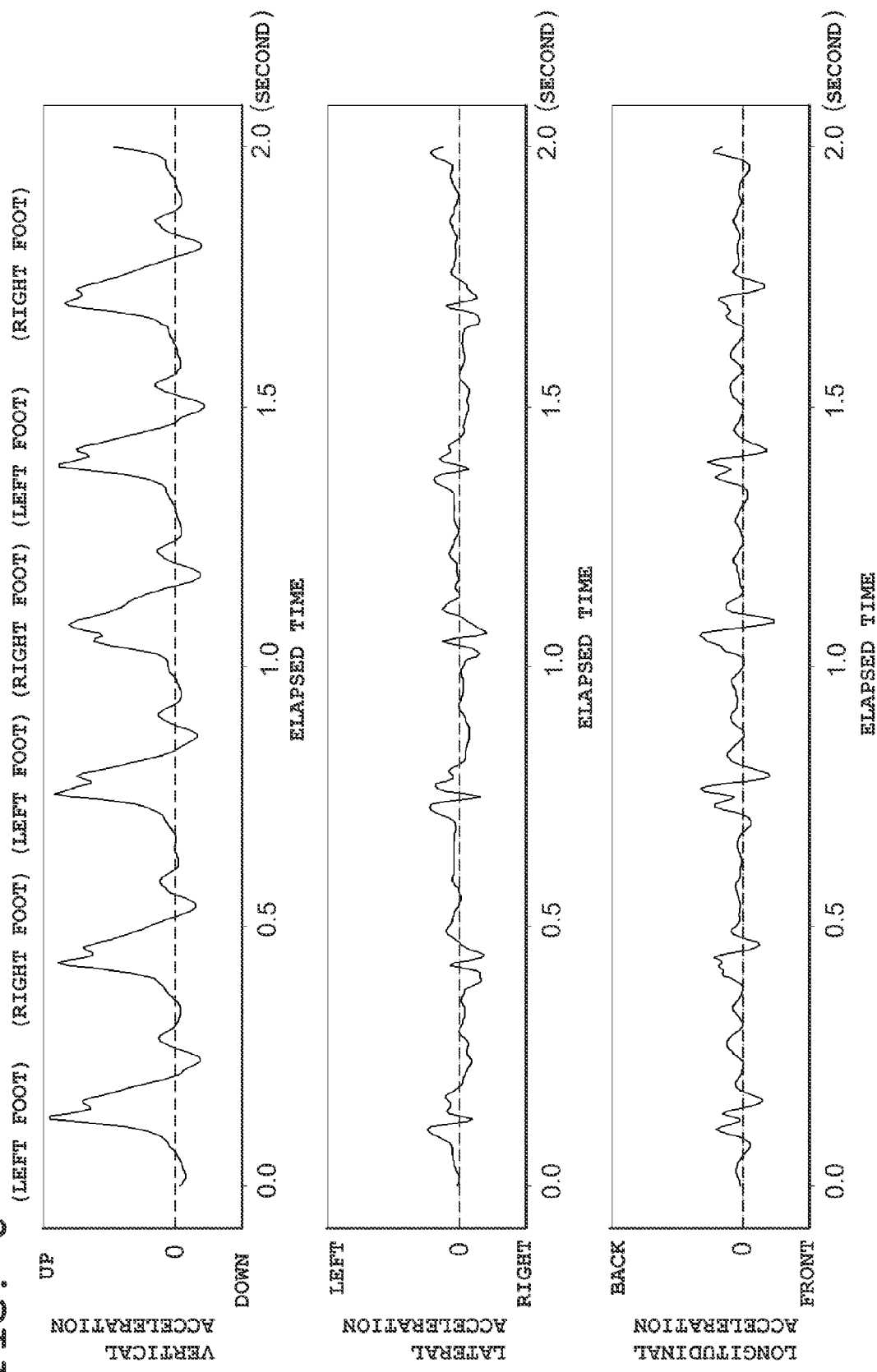
FIG. 6 is a signal waveform diagram of an example of acceleration signals in three axis directions obtained by the exercise support method according to the first embodiment.

FIG. 6 is a signal waveform diagram of an example of acceleration signals in three axis directions obtained by the exercise support method according to the present embodiment.

Figure 7:
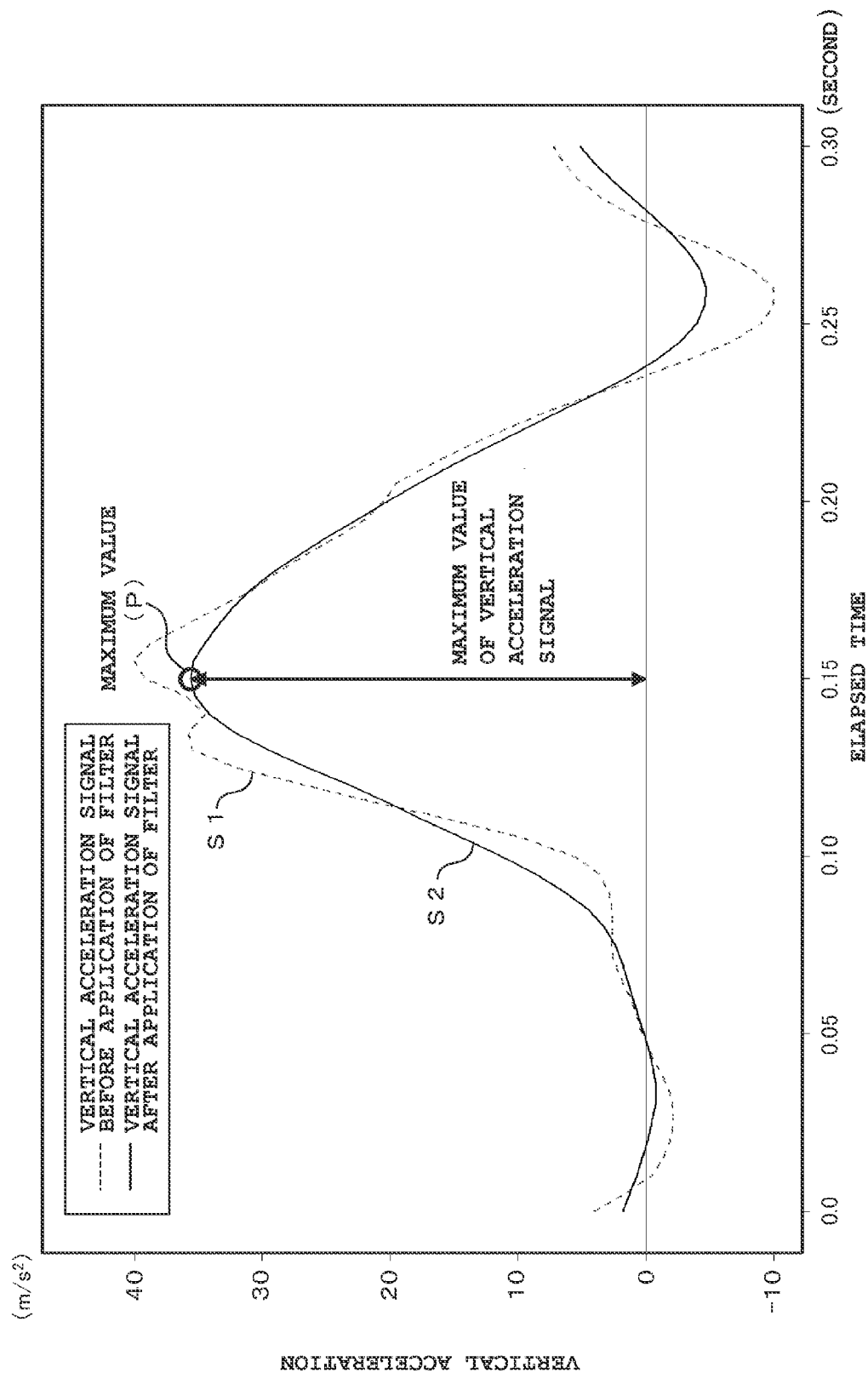
FIG. 7 is a diagram for describing the processing for obtaining the maximum value of an acceleration signal in a vertical direction, which is applied to the landing period estimation method according to the first embodiment.

FIG. 7 is a diagram for describing the processing for obtaining the maximum value of an acceleration signal in a vertical direction, which is applied to the landing period estimation method according to the present embodiment.

Figure 8:
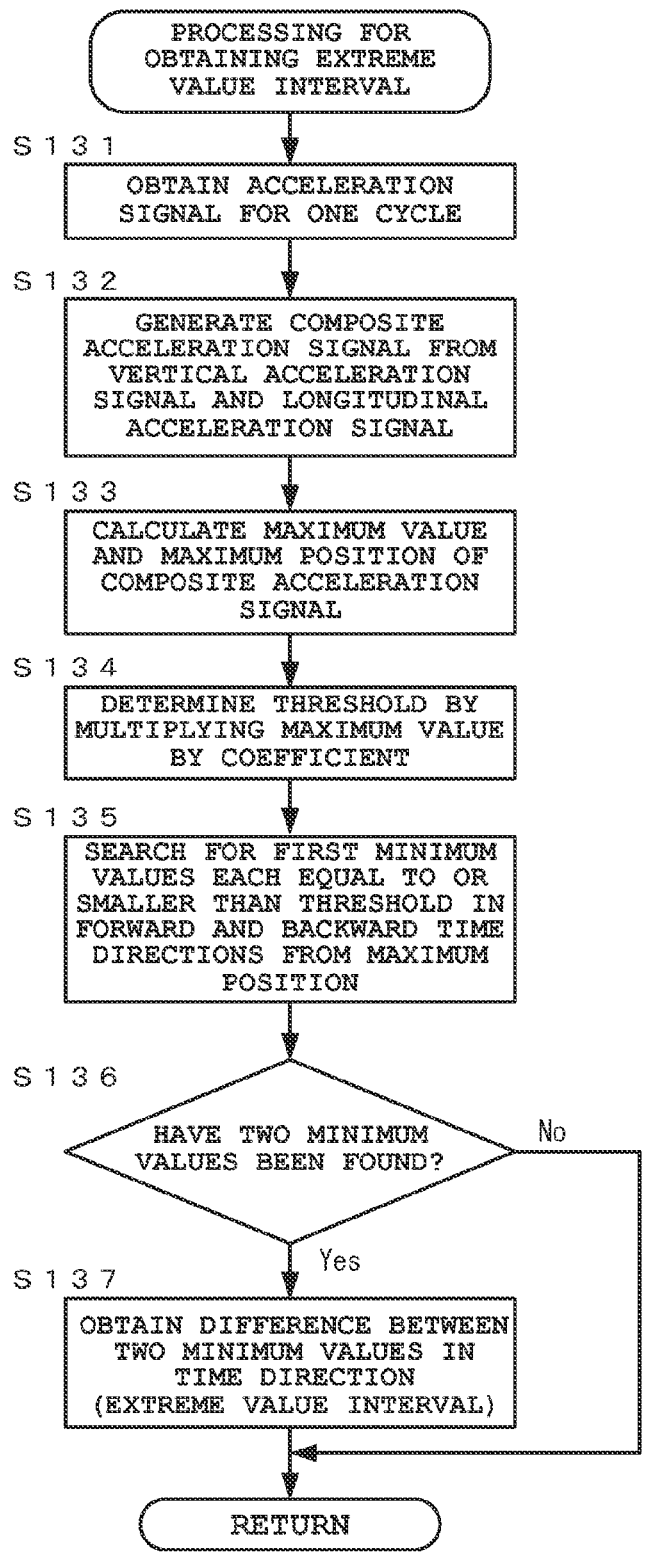
FIG. 8 is a flowchart of an example of processing for obtaining an extreme value interval, which is applied to the landing period estimation method according to the first embodiment.

FIG. 8 is a flowchart of an example of processing for obtaining an extreme value interval, which is applied to the landing period estimation method according to the present embodiment.

Figure 9:
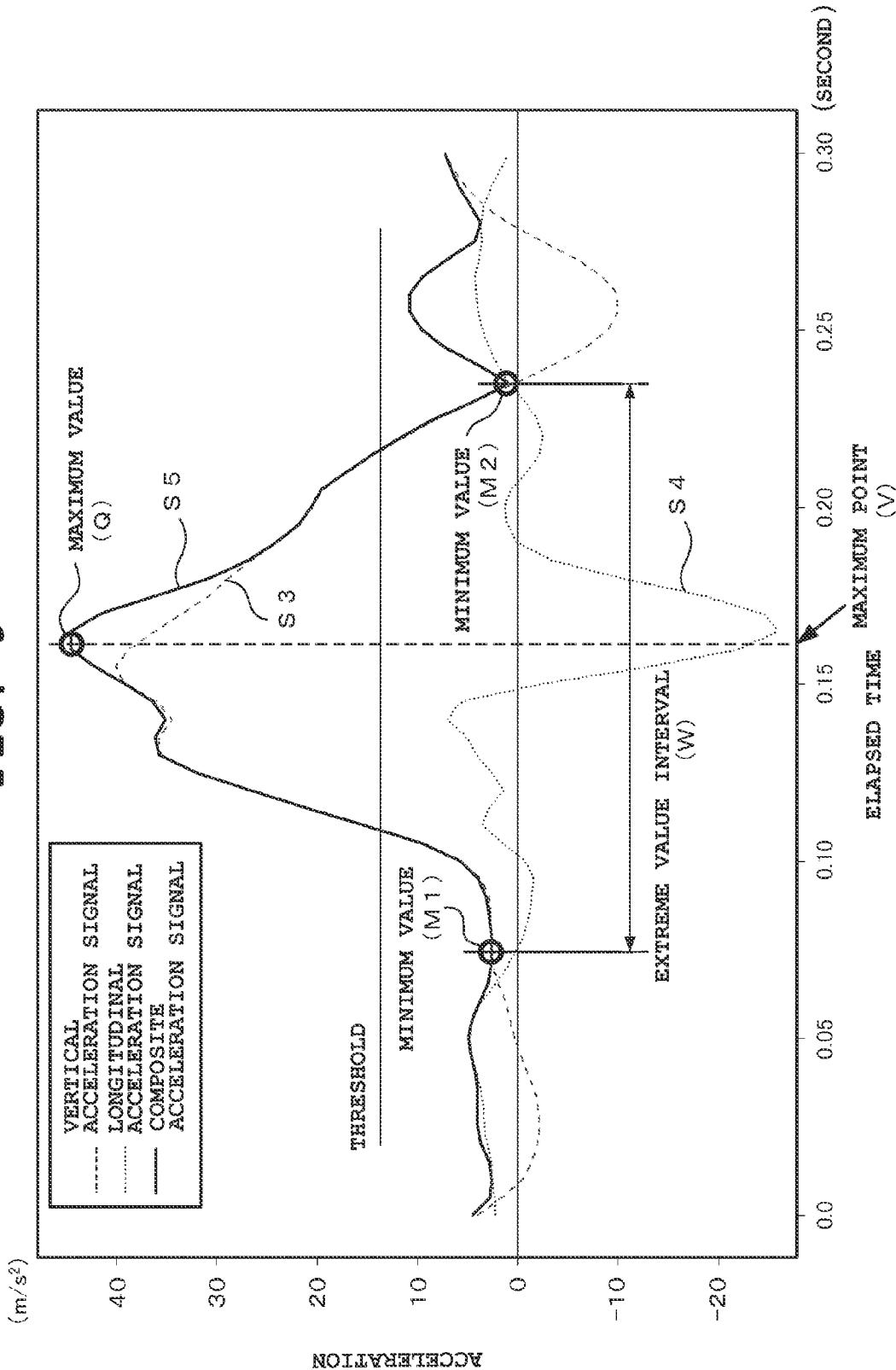
FIG. 9 is a diagram for describing the processing for obtaining an extreme value interval, which is applied to the landing period estimation method according to the first embodiment.

FIG. 9 is a diagram for describing the processing for obtaining an extreme value interval, which is applied to the landing period estimation method according to the first embodiment.

In the exercise support method according to the present embodiment, first, the user US operates the operation switch 140 of the chest device 100 mounted on the body, whereby the chest device 100 is powered ON to be activated (Step S101), as shown in the flowchart of FIG. 3, for example.

Then, the acceleration measuring section 110 of the chest device 100 starts a sensing operation. As a result, acceleration components in three axis directions while the user is exercising (while running) is detected and collected as acceleration signals (represented by "sensor data" in the drawing). These collected acceleration signals are stored as needed in a predetermined storage area of the storage section 130 in association with time data (Step S102).

Note that the sensing operation in the acceleration measuring section 110 may be performed intermittently or continuously.

Next, based on the collected acceleration signals, the signal processing section 124 of the computation processing circuit 120 performs processing in accordance with a predetermined algorithm program, and thereby performs processing for estimating a foot landing period as described below (Step S103).

Specifically, in the landing period estimation processing, the signal processing section 124 performs processing for obtaining the maximum value of vertical acceleration (Step Sill), processing for obtaining an extreme value interval (Step S112), and landing period calculation processing (Steps S113, S114 and S115), as shown in the flowchart of FIG. 4.

(Processing for Obtaining Maximum Value of Vertical Acceleration)

In the processing for obtaining the maximum value of vertical acceleration, specifically, the signal processing section 124 first extracts and obtains, from the collected acceleration signals in the three axis directions, an acceleration signal in the vertical direction for one cycle (one footstep) in the cyclic motion of a feet while exercising (Step S121), as shown in the flowchart of FIG. 5.

As a method for extracting an acceleration signal for one cycle (one footstep), for example, the following method can be adopted.

Generally, it is known that, in a running motion such as a running exercise, an acceleration signal in a vertical direction, such as that among the acceleration signals (raw data) in the three axis directions obtained by the acceleration measuring section 110, particularly shows a cyclic signal waveform for each footstep of left and right feet, as shown in an upper portion of FIG. 6.

Accordingly, by setting a specific base point in the signal waveform of the acceleration signal in the vertical direction, an acceleration signal for one footstep of the right foot or the left foot can be cut out (extracted).

Note that the acceleration signals in the three axis directions in FIG. 6 have been provided with the annotations "right foot" and "left foot" in accordance with the cycles of the signal waveforms, so as to explain each signal waveform for each footstep of the right foot or the left foot. However, the order of the right foot and the left foot may be reversed.

In the present embodiment, for example, a method can be used in which a cyclically appearing time period (for example, average time) between maximum values of an acceleration signal in a vertical direction is defined as one cycle, the time point of each maximum value is taken as a center (base point), and an acceleration signal for each half cycle in the forward and backward directions (+ direction and − direction) of the time axis is extracted.

An example of the signal waveform of the obtained vertical acceleration signal for one cycle is represented by a dotted line S1 in FIG. 7.

In FIG. 7, one cycle is 0.30 seconds, and a signal waveform for one cycle is shown which has been acquired by an acceleration signal in the range of a half time of one cycle (0.15 seconds) in each of the forward direction and the backward direction of a time axis being extracted with a time point (0.15 seconds) where vertical acceleration substantially has a maximum value as a base point.

At Step S122, the signal processing section 124 applies a moving-average filter of a predetermined size to the acceleration signal in the vertical direction for one cycle obtained at Step S121 (Step S122).

Here, the moving-average filter is applied to the acceleration signal on the basis of verification results that an actual foot landing period is more reflected when the acceleration of a movement average value for a certain amount of time period is taken into consideration rather than the acceleration of a certain instant (a short time period).

The optimum value of the size of the moving-average filter to be applied herein varies depending on each user. However, according to verification by the inventor, favorable results are obtained by a filter of a size from, when the length of one cycle (length from the time when one foot lands to the time when the other foot lands) is taken as 1, 0.2 to 0.4 being applied.

An example of the signal waveform of the acceleration signal in the vertical direction to which the above-described moving-average filter has been applied is represented by a solid line S2 in FIG. 7.

At Step S123, the signal processing section 124 obtains a maximum value (P) of the acceleration signal in the vertical direction to which the moving-average filter has been applied by Step S122 (Step S123), as shown in FIG. 7.

The obtained maximum value (P) of the acceleration signal is stored in a predetermined storage area of the storage section 130, and then the above-described processing for obtaining the maximum value of the vertical acceleration ends.

(Processing for Obtaining Extreme Value Interval)

Next, in the processing for obtaining an extreme value interval, specifically, the signal processing section 124 first extracts and obtains acceleration signals in the three axis directions for one cycle (one footstep) from the collected acceleration signals in the three axis directions (Step S131), as shown in the flowchart of FIG. 8.

As a method for extracting acceleration signals for one cycle (one footstep), for example, a method equivalent to that at Step S121 described above can be adopted.

An example of the signal waveform of a vertical acceleration signal for one cycle extracted as described above is represented by a rough dot line S3 in FIG. 9, and an example of the signal waveform of a longitudinal acceleration signal extracted as described above is represented by a fine dot line S4 in FIG. 9.

At Step S132, the signal processing section 124 combines the acceleration signal in the vertical direction (vertical acceleration) and the acceleration signal in the longitudinal direction (longitudinal acceleration) among the acceleration signals in the three axis directions for one cycle obtained at Step S131 so as to generate a composite acceleration (Step S132).

Specifically, the signal processing section 124 generates a composite acceleration based on the following Equation (1).

$$\text{Composite acceleration} = ((\text{vertical acceleration})^2 + (\text{longitudinal acceleration})^2)^{1/2} \quad (1)$$

An example of the signal waveform of the generated composite acceleration signal is represented by a solid line S5 in FIG. 9.

Next, the signal processing section 124 obtains a maximum value (Q) of the composite acceleration signal generated at Step S132, and a time point (maximum point: V) at which the composite acceleration signal has the maximum value (Step S133), as shown in FIG. 9.

The obtained maximum value (Q) of the composite acceleration signal and the time point (maximum point: V) at that time are stored in a predetermined storage area of the storage section 130.

Next, by multiplying the maximum value (Q) obtained at Step S133 by a predetermined coefficient, the signal processing section 124 determines a threshold for use in processing for searching for a change point regarding foot landing and takeoff (Step S134).

According to verification by the inventor, favorable results can be obtained here by the coefficient being set at a value around 0.2.

The value of this coefficient is not limited to 0.2, and can be set as needed depending on various conditions. For example, an arbitrary value can be selected as the coefficient from a predetermined range of numerical values including a specific center location, or a fixed value set in advance may be used.

Then, the signal processing section 124 searches for first minimum values (change points: M1 and M2) of the composite acceleration signal which are each equal to or smaller than the above-described threshold in forward and backward directions on the time axis, with the time point (maximum point: V) of the maximum value (Q) obtained at Step S133 as a base point (Step S135), as shown in FIG. 9.

The minimum values to be searched for correspond to change points regarding foot landing and takeoff in the composite acceleration signal for one cycle (one footstep).

According to verification by the inventor, by minimum values searched for as described above being applied as change points regarding foot landing and takeoff motions, an extremely high correlation can be found between an estimated foot landing period and an actual foot landing period, as described in verification of operations and effects described below (refer to FIG. 11).

In the present embodiment, a method has been described in which a threshold obtained by multiplying the maximum value (Q) of the composite acceleration signal by the predetermined coefficient is used to search for minimum values of the composite acceleration signal. However, the present invention is not limited thereto, and change points regarding foot landing and takeoff motions in the composite acceleration signal may be searched for by using another method.

At Step S136, the signal processing section 124 judges whether minimum values of the composite acceleration signal have been found by this search at two paired areas in both forward and backward directions on the time axis, with the maximum position (V) as a base point (Step S136).

Here, when judged that minimum values have not been found in the forward and backward directions on the time axis, the signal processing section 124 ends the above-described processing for obtaining an extreme value interval.

On the other hand, when judged that minimum values M1 and M2) have been found in the forward and backward directions on the time axis as shown in FIG. 9, the signal processing section 124 obtains an extreme value interval (change point interval, W), which is a difference between the two minimum values (M1 and M2) (Step S137).

The obtained extreme value interval (W) of the composite acceleration signal is stored in a predetermined storage area of the storage section 130, and then the above-described processing for obtaining the extreme value interval ends.

In the processing for obtaining an extreme value interval in the present embodiment, a composite acceleration signal formed of acceleration signals in vertical and longitudinal directions from among acceleration signals in three axis directions are used to obtain an extreme value interval.

This is based on verification by the inventor that minimum values can be searched for and obtained most stably with the use of a combination of acceleration signals in vertical and longitudinal directions.

Here, this combination of acceleration signals in a plurality of axis directions may include an acceleration signal in a lateral direction. However, the acceleration in the lateral direction tends to significantly vary among individuals and may not reflect an actual foot landing period. Therefore, it has been excluded from targets for composite acceleration.

However, in some cases, the acceleration signal in the lateral direction may reflect an actual foot landing period, depending on the way of running of the user US who is a measurement target, etc.

Accordingly, in the present invention, the combination of acceleration signals to be applied to the processing for obtaining an extreme value interval is not limited, and a composite acceleration signal including acceleration signal in two or more axis directions can be applied.

(Landing Period Calculation Processing)

Next, in the landing period calculation processing, specifically, the signal processing section 124 first judges whether an extreme value interval (W) has been obtained in the processing for obtaining an extreme value interval at Step S112 (Step S113), as shown in the flowchart of FIG. 4, for example.

When judged that an extreme value interval (W) has been obtained, the signal processing section 124 calculates a foot landing period by the following Equation (2) (first formula) based on coefficients a1, b1, and c1 and the maximum value (P) and the extreme value interval (W) of the acceleration signal in the vertical direction (Step S114).

$$\text{Foot landing period} = a1 \times \text{maximum value of vertical acceleration} + b1 \times \text{extreme value interval} + c1 \times \text{maximum value of vertical acceleration} \times \text{extreme value interval} \quad (2)$$

In Equation (2) above, when the unit of the foot landing period and the extreme value interval is set as [second] and the unit of the maximum value (P) of the acceleration signal in the vertical direction is set as [m/s$^2$], optimum values of the coefficients a1, b1, and c1 when 360 samples of twelve different test subjects are used are represented as follows.

a1=0.0070 (0.0063 to 0.0158)
b1=1.5270 (1.4584 to 1.8768)
c1=−0.0746 (−0.1404 to −0.0688)

Here, numerical values in parentheses in each of the coefficients a1, b1, and c1 indicate a range of an optimum value for each of these twelve test subjects.

Normally, the signs of the coefficients a1 and b1 are positive, and the sign of the coefficient c1 is negative.

The units of the respective coefficients a1, b1, and c1 vary. The coefficient a1 has a unit by which the unit of [a1 × maximum value of vertical acceleration] is time, b1 has a unit by which the unit of [b1× extreme value internal] is time, and c1 has a unit by which the unit of [c1× maximum value of vertical acceleration× extreme value interval] is time.

The test subjects for deriving the above-described coefficients a1, b1, and c1 are people enthusiastic about participating in competitions, such as those who have full-marathon experiences and those who are aiming to participate in marathon races.

By contrast, in the case of people not aiming to participate in marathon races, beginning runners (beginners), etc., coefficients with appropriate numerical values are applied based on their skill levels, running characteristics, physical strengths, and the like.

Accordingly, plural types of coefficients, such as a beginner mode and a race mode, may be prepared in advance, and the coefficients for calculating a foot landing period may be switched as needed based on the user's skill level, running characteristics, physical strength, and the like.

Equation (2) can be transformed into the following Equation (3), $$\text{Foot landing period} = b1 \times \text{extreme value interval} + \text{maximum value of vertical acceleration} \times (c1 \times \text{extreme value interval} + a1) \quad (3)$$

In the range of the numeral values of the coefficients a1, b1, and c1 described above, the first term (b1× extreme value interval) in Equation (3) is always larger than an actual foot landing period, and the second term (maximum value of vertical acceleration× (c1× extreme value interval+a1)) always has a negative value.

The reason for this is assumed that the foot landing period and the acceleration in the vertical direction tend to move oppositely. That is, when the foot landing period is short, the acceleration in the vertical direction is large, and the extreme value interval (W) is adjusted by these movements in opposite directions.

At Step S113, when judged an extreme value interval (W) has not been obtained, the signal processing section 124 calculates a foot landing period by the following Equation (4) (second formula) based on a coefficient a2 and the maximum value (P) of the acceleration signal in the vertical direction (Step S115).

$$\text{Foot landing period} = a2 \times (1/\text{maximum value of vertical acceleration}) \quad (4)$$

In Equation (4) above, when the unit of the foot landing period is set as [second] and the unit of the maximum value (P) of the acceleration signal in the vertical direction is set as [m/s$^2$], an optimum value of the coefficient a2 when 360 samples of twelve different test subjects are used is represented as follows, as with the above-described case.

a2=0.0169 (0.0109 to 0.0267)

Here, numerical values in parentheses in the coefficient a2 indicate the range of an optimum value for each of these twelve test subjects.

In this case as well, the landing period and the vertical acceleration tend to move oppositely.

The coefficient a2 has a unit by which [a2× (1/maximum value of vertical acceleration)] is time.

According to the inventor's verification regarding foot landing periods calculated (estimated) as described above, the foot landing period calculated at Step S114 (by use of Equation (2) or Equation (3)) reflects an actual foot landing period more than the foot landing period calculated at Step S115 (by use of Equation (4)).

Next, returning to the flowchart of FIG. 3, the computation processing circuit 120 performs analysis processing on the foot landing period calculated in the landing period estimation processing (Step S103) (Step S104).

Specifically, for example, the judging section 126 of the computation processing circuit 120 analyzes the calculated foot landing period itself to judged whether the foot landing period does not exceed a reference value (or a reference range) set in advance, and analyzes to judge whether a predetermined or more amount of change has occurred in an average value of foot landing periods obtained while exercising.

The judging section 126 compares various exercise information (for example, a fatigued state, the way of running, a moving speed, and an energy consumption amount) derived based on the calculated foot landing periods with a reference value (or a reference range) set in advance, and thereby determines the appropriateness of these pieces of exercise information.

Then, when the foot landing periods and the various exercise information indicate a specific state (for example, an abnormal state) as a result of these analyses, the judging section 126 generates a notification signal based on the judgment results and outputs the notification signal to the notifying section 150.

The analysis data and the judgment results generated in the above-described analysis processing are stored in a predetermined storage area of the storage section 130.

Next, the notifying section 150 generates predetermined vibration information and sound information based on the notification signal outputted from the computation processing circuit 120, and notifies the user US of the judgment results of the analysis processing described above (in particular, an abnormal state) as exercise support information (Step S105).

As a result, the exercise support information is tactually and aurally provided to the user US, whereby the user US can unfailingly recognize the foot landing periods and the change or abnormality of the various exercise information on a substantially real-time basis while exercising.

Next, the control section 122 of the computation processing circuit 120 judges whether to end the above-described series of processing (Step S106).

Specifically, the control section 122 of the computation processing circuit 120 judges, for example, whether the user US has turned the chest device 100 OFF or whether the user US has performed an operation for stopping the sensing operation in the acceleration measuring section 110 (whether a device stop instruction has been provided).

When judged that a device stop instruction has not been provided, the control section 122 returns to Step S102 and repeatedly performs the series of processing of the exercise support method described above (Steps S102 to S105).

Conversely, when judged that a device stop instruction has been provided, the control section 122 ends the above-described exercise support method.

(Operations and Effects)

Next, operations and effects of the above-described exercise support device and exercise support method are verified.

FIG. 10A and FIG. 10B are diagrams showing a relation between a foot landing period (actual foot landing period) found based on ground reaction force by use of a force plate and acceleration in a vertical direction.

Figure 11:
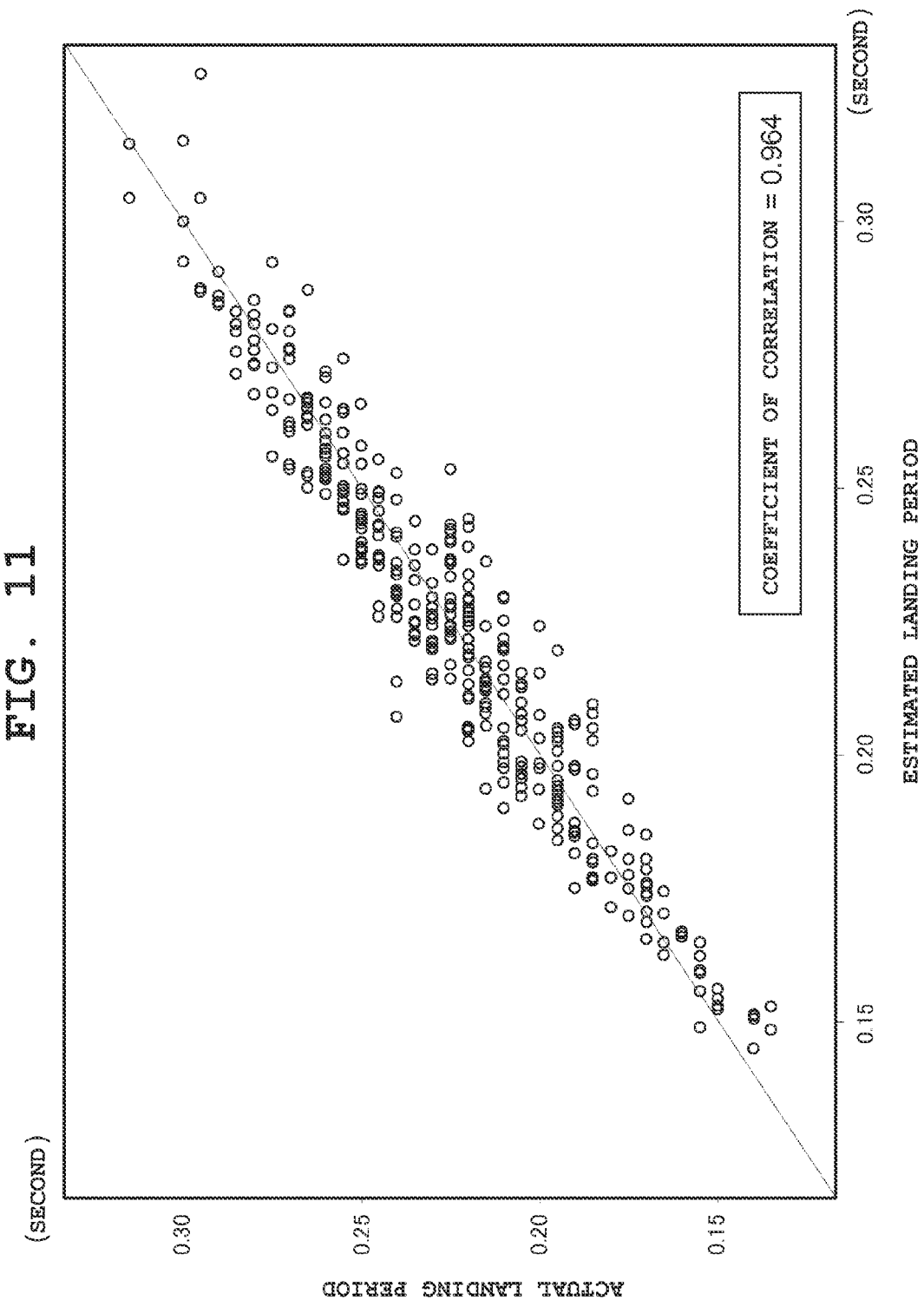
FIG. 11 is a diagram showing a relation between a foot landing period calculated in the first embodiment and an actual foot landing period.

FIG. 11 is a diagram showing a relation between a foot landing period calculated in the present embodiment and an actual foot landing period.

As shown in FIGS. 10A and 10B, ground reaction force obtained using a force plate indicates a value of substantially zero when the user who is a measurement target is not on the force plate (that is, the weight of the user has not been exerted on the force plate), and indicates a force added in each axis direction when the user is on the force plate (that is, the weight has been exerted on the force plate).

In FIG. 10A, a force exerted in a vertical direction is shown. Here, the time when ground reaction force exceeds a predetermined value (here, 0 [N]) from the vicinity of zero is defined as foot landing timing, and the time when the ground reaction force goes below the predetermined value is defined as foot takeoff timing. Also, a time between these landing timing and takeoff timing is defined as a foot landing period.

On the other hand, an acceleration signal in a vertical direction obtained by the acceleration measuring section 110 included in the chest device 100 worn on the chest is represented by a signal waveform such as that shown in FIG. 10B. This signal waveform tends to change in a manner similar to that of the ground reaction force of FIG. 10A as a whole.

However, when these are verified in detail, the signal waveforms are confirmed to have a significant difference particularly at time points corresponding to the foot landing and the foot takeoff. The reason for this is assumed that a plurality of joints and muscles intervene between the foot landing on the ground and the chest where the chest device 100 (acceleration measuring section 110) has been worn, and the force received on the sole is dispersed in the course of transmission to the chest via these joints and the like, or changed due to another force externally added.

Accordingly, accurate calculation (estimation) of (estimate) a foot landing period based on the above-described definitions by use of only an acceleration signal measured at the chest is difficult.

Thus, in the present embodiment, based on acceleration signals in three axis directions measured by the acceleration measuring section 110 worn on the chest of a human body, the maximum value (P) of a vertical acceleration signal for one cycle (one footstep) at the time of exercise and the extreme value interval (W) are obtained, as described above. The extreme value interval (W) indicates a period of time between two extreme values which are closest to each other and equal to or smaller than a predetermined threshold before and after the time point of the maximum value in a composite acceleration signal generated from acceleration signals in two or more axis directions for one cycle.

When the extreme value interval is obtained, a foot landing period is calculated by using the formula (Equation (2)) in which these feature amounts (P and W) are each multiplied by a predetermined coefficient and then added together.

On the other hand, when the extreme value interval is not obtained, a foot landing period is calculated by using the formula (Equation (4)) in which the maximum value (P) of the acceleration signal in the vertical direction is multiplied by a predetermined coefficient.

A correlation between a foot landing period calculated (estimated) as described above and a foot landing period (actual foot landing period) calculated based on ground reaction force is represented as in FIG. 11.

Here, a correlation distribution between estimated foot landing periods and actual fool landing periods of 360 samples of twelve different test subjects is shown, as with the case described above.

From verification of this correlation distribution shown in FIG. 11, the correlation therebetween is confirmed to be extremely high, and a coefficient of correlation of 0.964 is obtained.

That is, according to the present embodiment, a foot landing period can be accurately estimated based on acceleration signals measured at the chest.

In the present embodiment, the chest device 100 independently collects sensor data (acceleration signals) while exercising, and analyzes a calculated foot landing period and various exercise information. Then, when judged that the user US is in a specific state (such as an abnormal state), the chest device 100 provides exercise support information for notifying the user US of this state on a substantially real-time basis.

Therefore, only by wearing the exercise support device (chest device 100) having a simple structure, the user US can recognize change, abnormality, and the like of a foot landing period and various exercise information on a substantially real-time basis while exercising, and quickly reflect them to improve the current exercise status.

In the present embodiment, the notifying section 150 notifies the user US of judgment results of analysis processing based on sensor data obtained while exercising on a substantially real-time basis. However, the present invention is not limited thereto.

That is, the chest device 100 of the present embodiment may further include an interface section for transferring various data to an external information processing device (such as a personal computer, a smartphone, or a tablet terminal not shown in the drawings).

In this case, a configuration may be adopted in which a foot landing period and various exercise information calculated based on sensor data obtained while exercising and judgment results of analysis processing therefor are transferred to the information processing device via the interface section after the end of the exercise, and then displayed on a display section or the like of the information processing device as numerical value data, a graph or the like.

As a result, change tendencies of a foot landing period and various exercise information and the like can be visually provided to the user US. Therefore, the user US can intuitively grasp his or her own exercise status and effectively reflect them in future exercises.

Note that the interface section included in the chest device 100 will be described in detail in a third embodiment.

Also, in addition to the structure shown in FIG. 2, the chest device 100 of the present embodiment may have a structure including a heart rate measuring section which obtains heart rate data (biological information) of the user US while exercising and a GPS (Global Positioning System) reception circuit which obtains a current position or the like (geographic information) of the user US by using a GPS.

The biological information and the geographic information obtained by the heart rate measuring section and the GPS reception circuit are used when, for example, a state of the user US having abnormal exercise load is judged by the judging section 126 of the computation processing circuit 120 or association with a calculated Coot landing period and various exercise information (such as a fatigued state, the way of running, a moving speed, and an energy consumption amount) is analyzed.

As a result, the degree of exercise load which changes a foot landing period and various exercise information can be analyzed.

<Second Embodiment>

Next, an exercise support device and an exercise support method according to a second embodiment of the present invention are described.

In the above-described first embodiment, acceleration signals in three axis directions obtained by the acceleration measuring section 110 are used as they are so as to perform the landing period estimation processing.

In the second embodiment, effects of the tilt of the upper body where the chest device 100 is worn and the like are corrected for acceleration signals in three axis directions obtained by the acceleration measuring section 110.

(Exercise Support Device)

Figure 12:
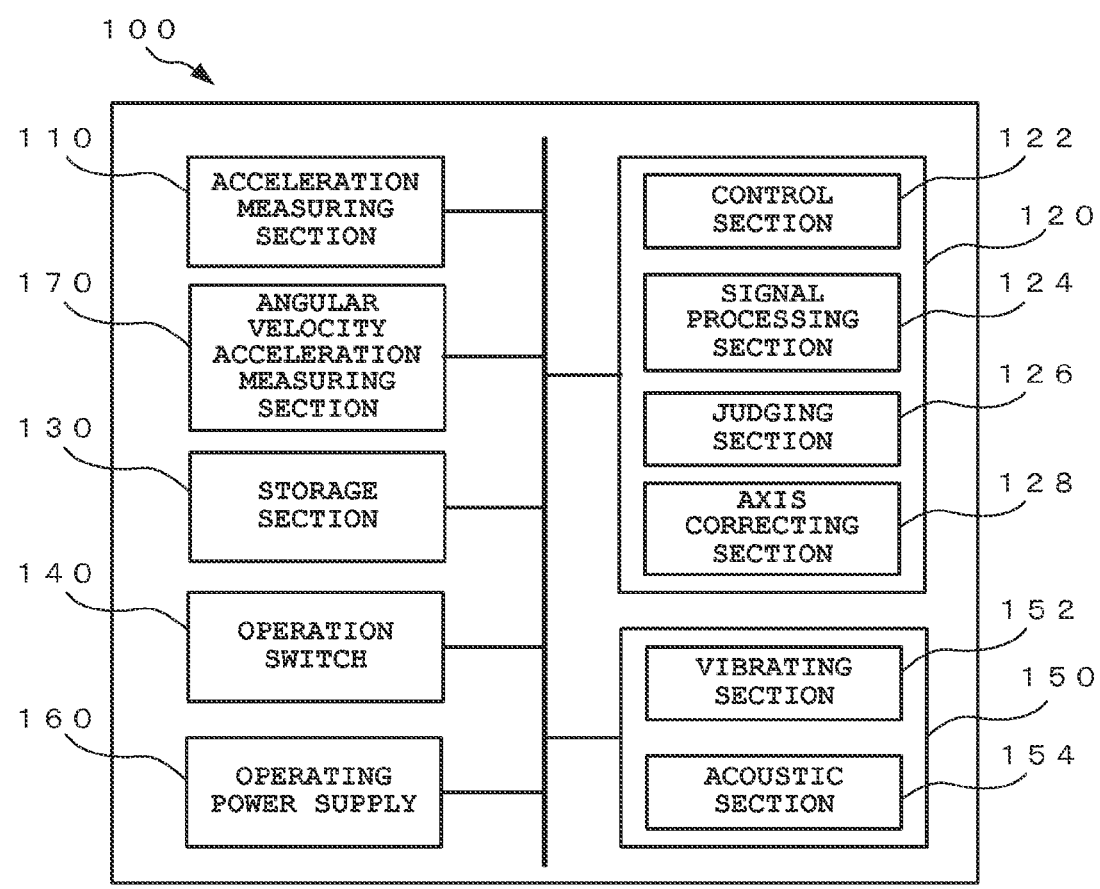
FIG. 12 is a functional block diagram showing an exercise support device according to a second embodiment of the present invention.

FIG. 12 is a functional block diagram showing the exercise support device according to the second embodiment of the present invention. Note that sections equivalent to those of the above-described first embodiment are provided with the same reference numerals and descriptions thereof are simplified.

The exercise support device according to the second embodiment has the same structure as that of the chest device 100 of the first embodiment shown in FIG. 2 except that an angular velocity measuring section 170 and an axis correcting section 128 have been added therein as shown in FIG. 12.

The angular velocity measuring section 170 measures change in a motion direction (angular velocity) while the user is exercising (running exercise).

In the present embodiment, the angular velocity measuring section 170, which has a triaxial angular velocity sensor, detects an angular velocity component occurring in a rotating direction of each of three axes orthogonal to one another shown in FIG. 1A and FIG. 1B and outputs the component as an angular velocity signal (angular velocity data).

The angular velocity signals in the rotating directions of the respective axes obtained by the angular velocity measuring section 170 are stored in a predetermined storage area of the storage section 130 in association with time data, and used in processing for correcting the axes of acceleration signals in the computation processing circuit 120 (axis correcting section 128).

The axis correcting section 128 is provided in the computation processing circuit 120. This axis correcting section 128 estimates a gravity direction from angular velocities measured by the angular velocity measuring section 170, and corrects the values of acceleration signals by rotating each axis of the acceleration signals so that the axis direction of the acceleration signal in the vertical direction measured by the acceleration measuring section 110 coincides with the gravity direction.

The acceleration signals in the respective axis directions corrected by the axis correcting section 128 are stored in a predetermined storage area of the storage section 130, and used when the maximum value (P) of the acceleration signal in the vertical direction and the extreme value interval (W) in the composite acceleration signal are obtained in the processing for estimating a foot landing period in the signal processing section 124 described above.

Note that the acceleration measuring section 110; the control section 122, the signal processing section 124, and the judging section 126 of the computation processing circuit 120; the storage section 130; the operation switch 140; the notifying section 150; and the operating power supply 160 have structures equivalent to those of the above-described first embodiment, and therefore are not described herein.

(Exercise Support Method)

Next, the exercise support method for the exercise support device according to the present embodiment is described.

Figure 13:
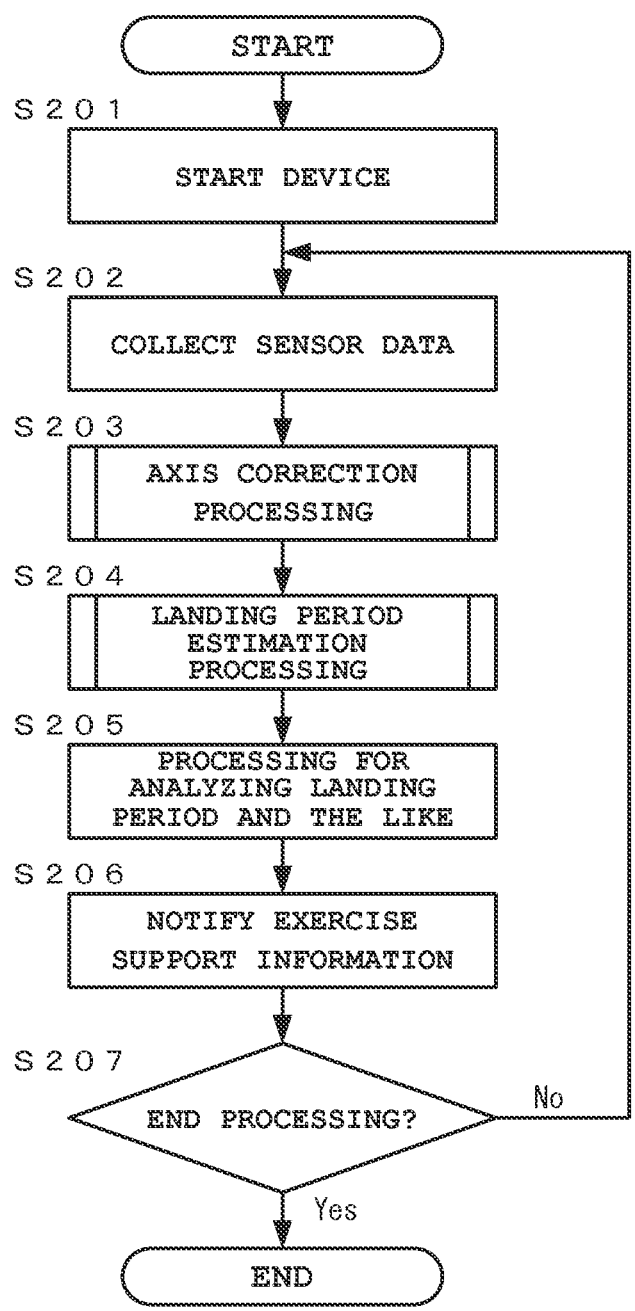
FIG. 13 is a flowchart of an example of an exercise support method to be performed for the exercise support device according to the second embodiment.

FIG. 13 is a flowchart of an example of the exercise support method to be performed for the exercise support device according to the present embodiment.

Note that description of procedures equivalent to those of the above-described first embodiment is simplified herein.

Figure 14:
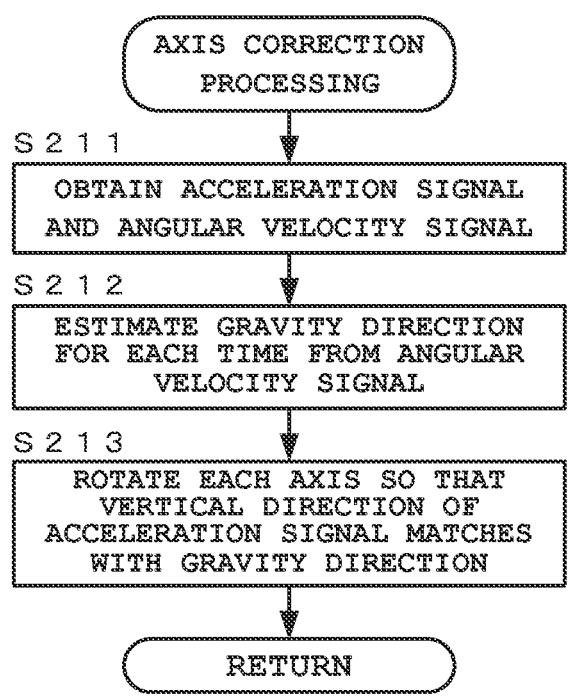
FIG. 14 is a flowchart of an example of processing for correcting the axes of acceleration signals, which is applied to the exercise support method according to the second embodiment.

FIG. 14 is a flowchart of an example of processing for correcting the axes of acceleration signals, which is applied in the exercise support method according to the present embodiment.

FIG. 15 is a signal waveform diagram of an example of acceleration signals in three axis directions corrected by the processing for correcting the axes of acceleration signals according to the present embodiment.

In the exercise support method according to the present embodiment, the user US first turns the chest device 100 on to activate it (Step S201), as shown in the flowchart of FIG. 13.

Next, the acceleration measuring section 110 and the angular velocity measuring section 170 of the chest device 100 starts a sensing operation, whereby acceleration signals and angular velocity signals (in the drawing, collectively referred to as "sensor data") while the user is exercising (running exercise) are collected, and stored as needed in a predetermined storage area of the storage section 130 in association with each other (Step S202).

Next, based on the collected acceleration signals and the angular velocity signals, the axis correcting section 128 of the computation processing circuit 120 performs processing in accordance with a predetermined algorithm program, and thereby performs processing for correcting the axes of the acceleration signals as follows (Step S203).

That is, in a motion sensor for detecting the exercise status of a human body, such as the acceleration measuring section 110 and the angular velocity measuring section 170 worn on the upper body (in particular, trunk) of a human body, a difference occurs between the gravity direction and the vertical direction of the sensor due to the tilt of the upper body or the like.

Since this difference in the axis direction is changed with time, the difference in the axis direction varying with time is required to be corrected based on measured values of acceleration and angular velocity.

Accordingly, in the present embodiment, the axis correcting section 128 first obtains acceleration signals and angular velocity signals for each clock time from the collected acceleration signals and angular velocity signals (Step S211), as shown in the flowchart of FIG. 14.

Next, the axis correcting section 128 estimates a gravity direction for each clock time from the angular velocity signals obtained, at Step S211 (Step S212).

Then, the axis correcting section 128 corrects the values of the acceleration signals in the respective axis directions by rotating each axis of the acceleration signals such that the gravity direction estimated at Step S212 coincides with the axis direction of the acceleration signal in the vertical direction (Step S213).

Specifically, when acceleration signals for a plurality of cycles are obtained while the user US is running at a constant speed and averaged, if the vertical direction of the sensor and the gravity direction coincide with each other, the average value of the acceleration signals in the lateral direction and the longitudinal direction is 0.

However, since gravity acceleration is added to the acceleration in the lateral and longitudinal directions due to the tilt of the body in the running motion, the above-described average value is not 0 in practice.

Thus, as an axis correction method, the axis correcting section 128 finds a tilt angle so that the average value of these axes is 0 (Step S212).

Then, the axis correcting section 128 calculates and applies a rotation matrix to the acceleration in each direction (Step S213) so as to correct the axes.

The acceleration signals in the three axis directions after the axis correction are represented, for example, as in FIG. 15.

Compared with the acceleration signals in the three axis directions before axis correction (raw data) shown in FIG. 6, the values of the acceleration have been changed in all of the axis directions. In particular, the acceleration signals in the lateral direction and the longitudinal direction have been significantly affected by the correction.

Note that the method for correcting the axes of the acceleration signals are not limited to the above method.

For example, the axis correction can be performed by estimating the gravity direction by calculating a time average of the acceleration signals.

Next, returning to the flowchart of FIG. 13, the signal processing section 124 performs landing period estimation processing including processing for obtaining a maximum value of vertical acceleration, processing for obtaining an extreme value interval, and landing period calculation processing as in the case of the above-described first embodiment (Step S204), based on the acceleration signals in the three axis directions corrected in the axis correction processing at Step S203.

As a result, the effect such as the tilt of the body in the running motion is inhibited (eliminated) and a foot landing period where an actual foot landing period has been reflected can be calculated (estimated) more accurately.

Next, the judging section 126 performs various analysis processing on the foot landing period calculated in the landing period estimation processing (Step S204), generates a notification signal based on these judgment results, and outputs it to the notifying section 150 (Step S205).

Then, based on the notification signal, the notifying section 150 generates predetermined vibration information and sound information, and thereby notifies the user US of exercise support information (Step S206).

As a result, the user US can unfailingly recognize the change and abnormality of the foot landing period and various exercise information tactually and aurally while exercising.

Next, the control section 122 judges whether to end the series of processing described above. When a judgment is made not to end the processing, the control section 122 returns to Step S202 and repeatedly performs the series of processing of the exercise support method (Steps S202 to S206). When a judgment is made to end the processing, the control section 122 ends the exercise support method.

As described above, in the present embodiment, even when the upper body of the user while exercising is tilted, an effect such as the tilt of the body can be inhibited (eliminated) based on sensor data (acceleration signals and angular velocity signals) measured at the chest, and a foot landing period where an actual foot landing period has been reflected can be calculated (estimated) more accurately.

That is, only by wearing the exercise support device having a simple structure, the user US can accurately grasp the change, abnormality, and the like of foot landing periods and various exercise information while exercising on a substantially real-time basis, and can quickly reflect them to improve the current exercise status.

In the present embodiment, angular velocity signals obtained by the angular velocity measuring section 170 are used for the correction of the axes of acceleration signals. However, the obtained angular velocity signals may be used for the following analysis in the judging section 126.

That is, in the above description of the first embodiment, the method has been described in which one cycle (one footstep) in cyclic foot movements while exercising is cut out based on an acceleration signal in a vertical direction. In this method, it is impossible to judge whether a motion for one footstep corresponds to a signal waveform related to a motion of swinging the right leg forward or to a signal waveform related to a motion of swinging the left leg forward.

In order to solve this problem, the polarity of angular velocity occurring on an axis in a vertical direction (gravity direction) in a predetermined period including timing at which the whole body weight is on one of the left and right feet is detected, and a direction in which the body while exercising is being rotated is judged. As a result, it is possible to judge whether the signal waveform of an acceleration signal represents a signal waveform related to a motion of swinging the right leg forward or represents a signal waveform related to a motion of swinging the left leg forward.

As a result of this configuration, by obtaining a foot landing period and various exercise information after associating an acceleration signal for one cycle cut out in the processing for obtaining a maximum value of vertical acceleration and the processing for obtaining an extreme value interval described above with a left or right leg motion judged by the left/right leg motion judgment processing described above, it is possible to judge the quality of the left-right balance and the exercise form (running form) of the user US while exercising.

<Third Embodiment>

Next, an exercise support device and an exercise support method according to a third embodiment of the present invention are described.

In the above-described first and second embodiments, the chest device 100 (single device) worn on the body independently estimates a foot landing period based on sensor data of the user US obtained while exercising, analyzes the change, abnormality, and the like of the foot landing period and various exercise information, and notifies the user US of exercise support information on a real-time basis when a specific state occurs. In the third embodiment, in addition to the chest device 100, a separate notifying device (separate device) that is worn on the body is provided, and results of judgment regarding the change, abnormality, and the like of a foot landing period and various exercise information are provided via this notifying device on a real-time basis.

(Exercise Support Device)

FIG. 16A and FIG. 16B are schematic diagrams of the exercise support device according to the third embodiment of the present invention.

Here, FIG. 16A is a schematic diagram showing a state where the exercise support device according to the present embodiment has been worn on a human body.

FIG. 16B is an external view of a structural example of the notifying device to be applied to the exercise support device according to the present embodiment.

Figure 17A:
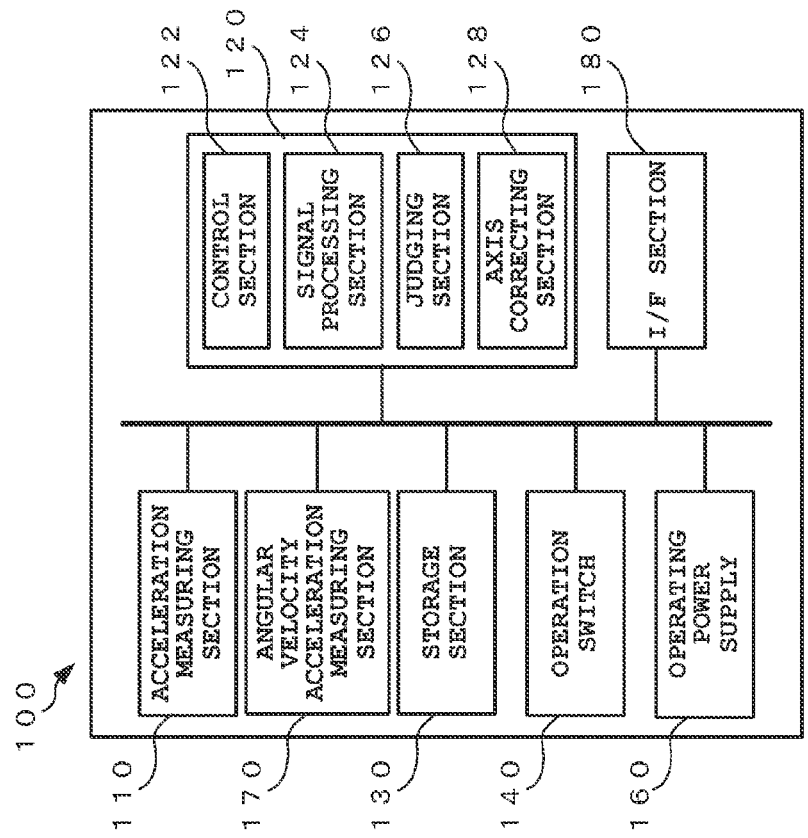
FIG. 17A and FIG. 17B are functional block diagrams each showing a structural example of a chest device to be applied to the exercise support device according to the third embodiment.
Figure 17B:
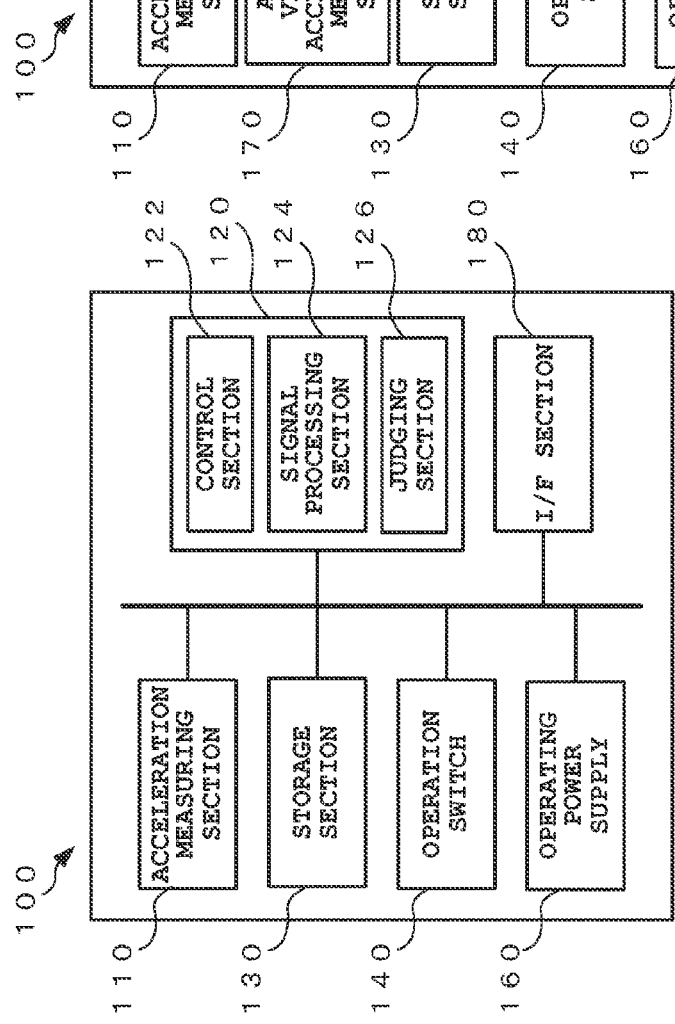

FIG. 17A and FIG. 17B are functional block diagrams each showing a structural example of a chest device to be applied to the exercise, support device according to the present embodiment.

Here, FIG. 17A is a functional block diagram showing a structural example of the chest device according to the present embodiment, and FIG. 17B is a functional block diagram showing another structural example of the chest device according to the present embodiment.

Figure 18:
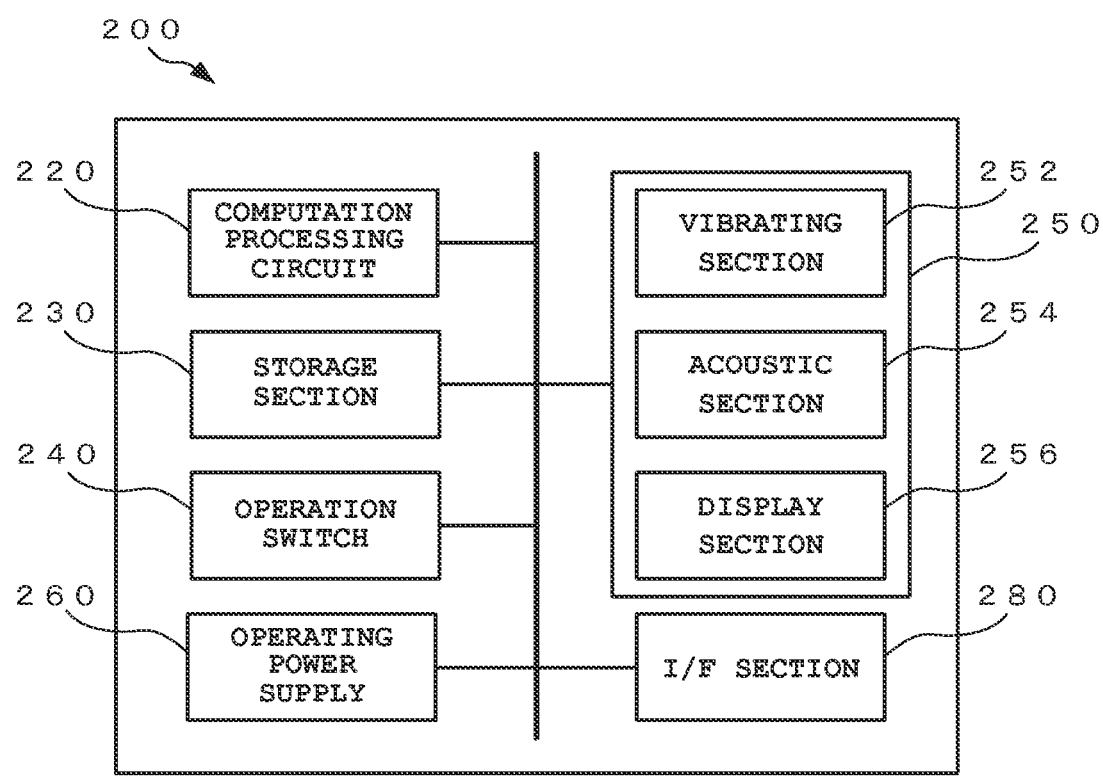
FIG. 18 is a functional block diagram showing a structural example of a notifying device to be applied to the exercise support device according to the third embodiment.

FIG. 18 is a functional block diagram showing a structural example of the notifying device to be applied to the exercise support device according to the present embodiment.

Note that sections equivalent to those of the above-described first embodiment are provided with the same reference numerals and descriptions thereof are simplified.

The exercise support device according to the third embodiment includes, for example, the chest device 100 that is worn on the chest of the user US, and a wristwatch-type or wristband-type notifying device (hereinafter referred to as a "wrist device" for convenience of explanation) 200 that is worn on a wrist (upper arm) or the like, as shown in FIG. 16A.

The chest device 100 has an outer appearance equivalent to that of the above-described first or second embodiment.

The wrist device 200 mainly includes, for example, a device body 201 that notifies the user US of at least the change, abnormality, and the like of a foot landing period and exercise information and a belt section 202 that is wound around a wrist of the user US so that the device body 201 is worn on the user US, as shown in FIG. 16B.

The chest device 100 (device body 101) has the same structure as those of the first and second embodiments (refer to FIG. 2 and FIG. 12) except that the notifying section 150 has been excluded and an interface section (in the drawing, represented as "I/F section") 180 has been provided therein, as shown in FIG. 17A and FIG. 17B.

Note that the chest device 100 may have a structure in which the I/F section 180 is provided in addition to the sections included in the first and second embodiments (refer to FIG. 2 and FIG. 12).

The acceleration measuring section 110, the computation processing circuit 120, the storage section 130, the operation switch 140, the operating power supply 160, and the angular velocity measuring section 170 have structures equivalent to those of the above-described first or second embodiment, and therefore are not described herein.

The I/F section 180 functions as at least a communication interface when a notification signal generated in accordance with judgment results of analysis processing regarding a foot landing period and various exercise information performed by the judging section 126 of the computation processing circuit 120 is transmitted to the wrist device 200.

In addition to the notification signal, the I/F section 180 may transmit to the wrist device 200 a foot landing period itself calculated by the signal processing section 124, various exercise information, and analysis data and judgment results generated in analysis processing in the judging section 126 and stored in the storage section 130.

As a method for transferring data, information, and the like between the chest device 100 and the wrist device 200 via the I/F section 180, various wireless communication methods such as Bluetooth (registered trademark) or WiFi (wireless fidelity (registered trademark)), and various wired communication methods via a communication cable such as a USB (Universal Serial Bus) cable can be adopted.

In the present embodiment, the control section 122 of the computation processing circuit 120 performs processing in accordance with a predetermined control program, and thereby controls a data transfer operation in the I/F section 180 in addition to various operations described in the above-described first or second embodiment.

Specifically, the wrist device 200 mainly includes, for example, a computation processing circuit 220, a storage section 230, an operation switch 240, a notifying section 250, an operating power supply 260, and an I/F section 280, as shown in FIG. 18.

The computation processing circuit 220, which is a computation processing device such as a CPU or MPU including a timing function, performs processing in accordance with the predetermined control program, and thereby controls an operation in each section, such as a notifying operation in the notifying section 250 described below and a data transfer operation in the I/F section 280, so as to achieve a predetermined function.

The storage section 230, which has a non-volatile memory, stores at least a notification signal transmitted from the chest device 100 in a predetermined storage area in association with time data.

In addition to this notification signal, the storage section 230 may store, in a predetermined storage area, a foot landing period and various exercise information transmitted from the chest device 100, and analysis data and judgment results generated in analysis processing therefor in association with time data.

Also, the storage section 230 may store a control program to be executed in the above-described computation processing circuit 220.

Note that a non-volatile memory portion constituting the storage section 230 may be partially or entirely a removable storage medium such as a memory card so as to be removable from the wrist device 200.

The operation switch 240 may be a push-button-type switch provided protruding from a side surface of the device body 201 as shown in FIG. 16B, or may be a touch-panel-type switch provided on the front surface side (visual field side) of a display section 256 of the notifying section 250 described below.

The operation switch 240 is used for various input operations, such as operation control when notifying exercise support information based on judgment results of analysis processing performed in the chest device 100, and settings of items to be displayed on the display section 256.

The notifying section (information providing section) 250 includes, for example, a vibrating section 252, an acoustic section 254, and the display section 256, as shown in FIG. 18.

The vibrating section 252 and the acoustic section 254, which have functions equivalent to those of the notifying section 150 of the chest device 100 described in the above-described first or second embodiment, generate predetermined vibration information and sound information based on at least a notification signal transmitted from the chest device 100, and thereby tactually and aurally notify the user US of exercise support information.

Here, the exercise support information provided from the vibrating section 252 and the acoustic section 254 may be provided in conjunction with the display of the display section 256.

The display section 256, which has a display panel, for example, a liquid-crystal-type or a light-emitting-element-type, that displays predetermined image information and character information, or emits light of light-emitting information such as a predetermined light-emission color or light-emission pattern based on at least a notification signal transmitted from the chest device 100, so that the user US is visually notified of exercise support information.

This display section 262 may display a foot landing period transmitted from the chest device and analysis data and judgment results generated in each analysis processing as they are as numerical value data or as graphs.

In addition, the display section 256 may display various information such as current time, running time, pitch, and lap time.

Note that the notifying section 250 may have a structure in which at least one of the vibrating section 252, the acoustic section 254, and the display section 256 has been provided.

The operating power supply 260 supplies driving electric power to each section of the wrist device 200 (device body 201).

As the operating power supply 260, a known primary battery or secondary battery, or a power supply an by energy harvest technology or the like can be applied, as with the operating power switch 160 of the above-described chest device 100.

The interface section 280 functions as at least a communication interface when a notification signal transmitted from the chest device 100 is received.

In addition to the notification signal, the interface section 280 may receive a foot landing period and various exercise information transmitted from the chest device 100, and their analysis data and judgment results generated in analysis processing.

(Exercise Support Method)

Next, the exercise support method for the exercise support device according to the present embodiment is described.

Here, the exercise support method when the chest device 100 having the structure shown in FIG. 17A is adopted is described. When the exercise support device has the structure shown in FIG. 17B, a substantially equivalent exercise support method is performed by using an axis-corrected acceleration signal.

Figure 19:
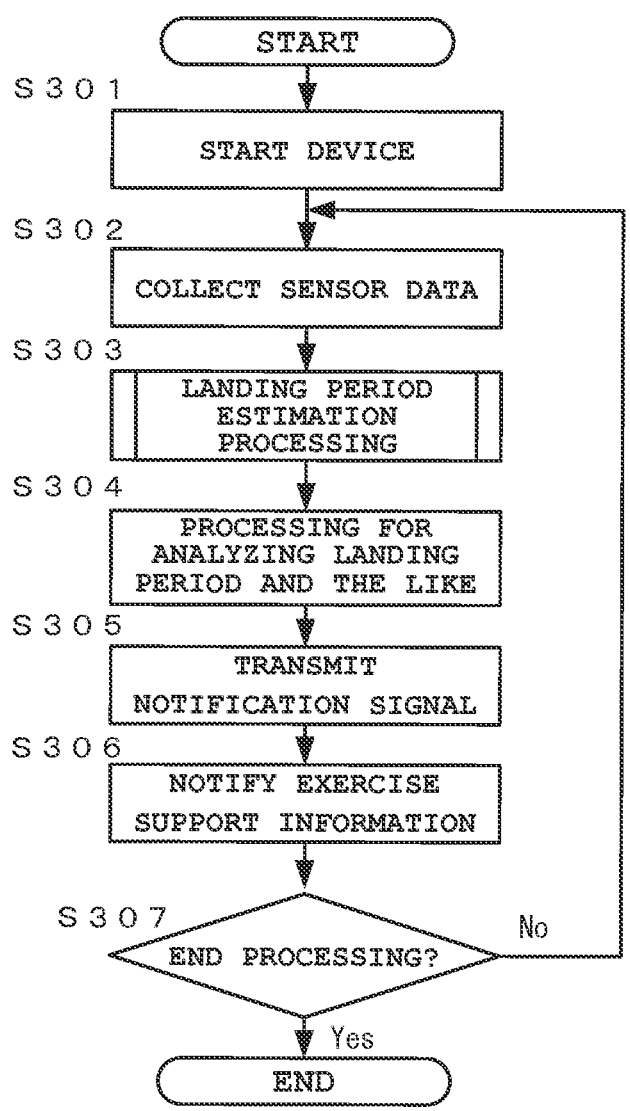
FIG. 19 is a flowchart of an example of an exercise support method to be performed for the exercise support device according to the third embodiment.

FIG. 19 is a flowchart of an example of the exercise support method to be performed for the exercise support device according to the present embodiment. Here, procedures equivalent to those of the above-described first or second embodiment are simplified.

In the exercise support method according to the present embodiment, the user US first turns on the chest device 100 and the wrist device 200 to activate them (Step S301), as shown in the flowchart of FIG. 19. As a result, an operation clock is synchronized between the chest device 100 and the wrist device 200.

Then, the chest device 100 starts a sensing operation in the acceleration measuring section 110, whereby sensor data (at least the acceleration signals) of the user US while exercising (while running) is collected, and stored as needed in a predetermined storage area of the storage section 130 (Step S302).

Next, as with the above-described first embodiment, the signal processing section 124 performs landing period estimation processing including processing for obtaining a maximum value of vertical acceleration, processing for obtaining an extreme value interval, and landing period calculation processing, based on the collected sensor data (Step S303).

As a result, an accurate foot landing period where the actual foot landing period has been reflected is calculated (estimated).

Next, the judging section 126 performs various analysis processing regarding the foot landing period calculated in the landing period estimation processing (Step S303) (Step S304).

Subsequently, the control section 122 generates a notification signal based on these analysis results, and transmits this notification signal as needed from the chest device 100 to the wrist device 200 via the I/F section 180 by, for example, a wireless communication method (Step S305).

Then, based on the notification signal transmitted from the chest device 100, the wrist device 200 generates predetermined vibration information, sound information, and display information from the notifying section 250 while exercising, and thereby notifies the user of exercise support information (Step S306).

As a result, the change, abnormality, and the like of the foot landing period and various exercise information can be reliably recognized by the user US tactually, aurally, and visually.

Next, the control section 122 judges whether to end the above-described series of processing. When judged not to end the processing, the control section 122 returns to Step S302 and repeatedly performs the series of processing of the exercise support method (Steps S302 to S306). When judged to end the processing, the control section 122 ends the exercise support method.

As described above, in the present embodiment, based on sensor data obtained while exercising by the chest device 100 worn on the chest of the user US, an accurate foot landing period where an actual foot landing period has been reflected is calculated (estimated), and a notification signal generated based on judgment results of analysis processing regarding the foot landing period and various exercise information is transmitted to the wrist device 200 on a wrist as needed.

Then, exercise support information based on the notification signal received by the wrist device 200 is provided to the user US on a substantially real-time basis.

Therefore, by the exercise support information provided from the wrist device 200 worn on the wrist, the user US can grasp the change, abnormality, and the like of the foot landing period and various exercise information while exercising on a substantially real-time basis and quickly correct the current exercise status.

In the present embodiment, a notification signal generated in accordance with judgment results of analysis processing regarding a foot landing period calculated based on sensor data obtained by the chest device 100 while exercising is transmitted to the wrist device 200 as needed, and notified to the user US as exercise support information on a substantially real-time basis. However, the present invention is not limited thereto.

That is, in the exercise support device of the present embodiment, a configuration may be adopted in which a foot landing period itself and various exercise information calculated in the chest device 100 and their analysis data and judgment results are transmitted to the wrist device 200 as needed and displayed on the display section 256 of the wrist device 200 as numerical value data, graphs, or the like.

As a result of this configuration, the change, abnormality, and the like of a foot landing period and various exercise information can be visually provided to the user US while exercising on a substantially real-time basis. Therefore, the user US can accurately grasp his or her own exercise status and quickly reflect it to improve the current exercise status.

Also, in the above descriptions of the present embodiment, the wrist device 200 that is worn on a wrist of the user US has been shown as an example of a notifying device that provides predetermined exercise support information to the user US based on a notification signal transmitted from the chest device 100. However the present invention is not limited thereto.

That is, any notifying device is applicable to the present embodiment as long as it can provide exercise support information through any human sense, such as eyesight, touch, or hearing.

Accordingly, devices of various forms, such as an earphone type or earpiece type that is worn on an ear, a necklace type that is worn on the neck, and a sports-glasses type shaped in eyeglasses may be adopted as a notifying device. Also, this device may be included in a smartphone and worn on an upper arm.

<Fourth Embodiment>

Next, an exercise support device and exercise support method according to a fourth embodiment of the present invention are described.

In the above-described first to third embodiments, a foot landing period is estimated based on sensor data of the user US obtained by the chest device 100 while exercising, the change, abnormality, and the like of the foot landing period and various exercise information are analyzed, and a notification signal according to the judgment results is generated.

In the fourth embodiment, the sensor data obtained by the chest device 100 is transferred to an external information processing device (separate device). Then, in this external information processing device, a foot landing period is estimated, the change, abnormality, and the like of the foot landing period and various exercise information are analyzed, and exercise support information according to the judgment result is notified to the user US.

(Exercise Support Device)

Figure 20:
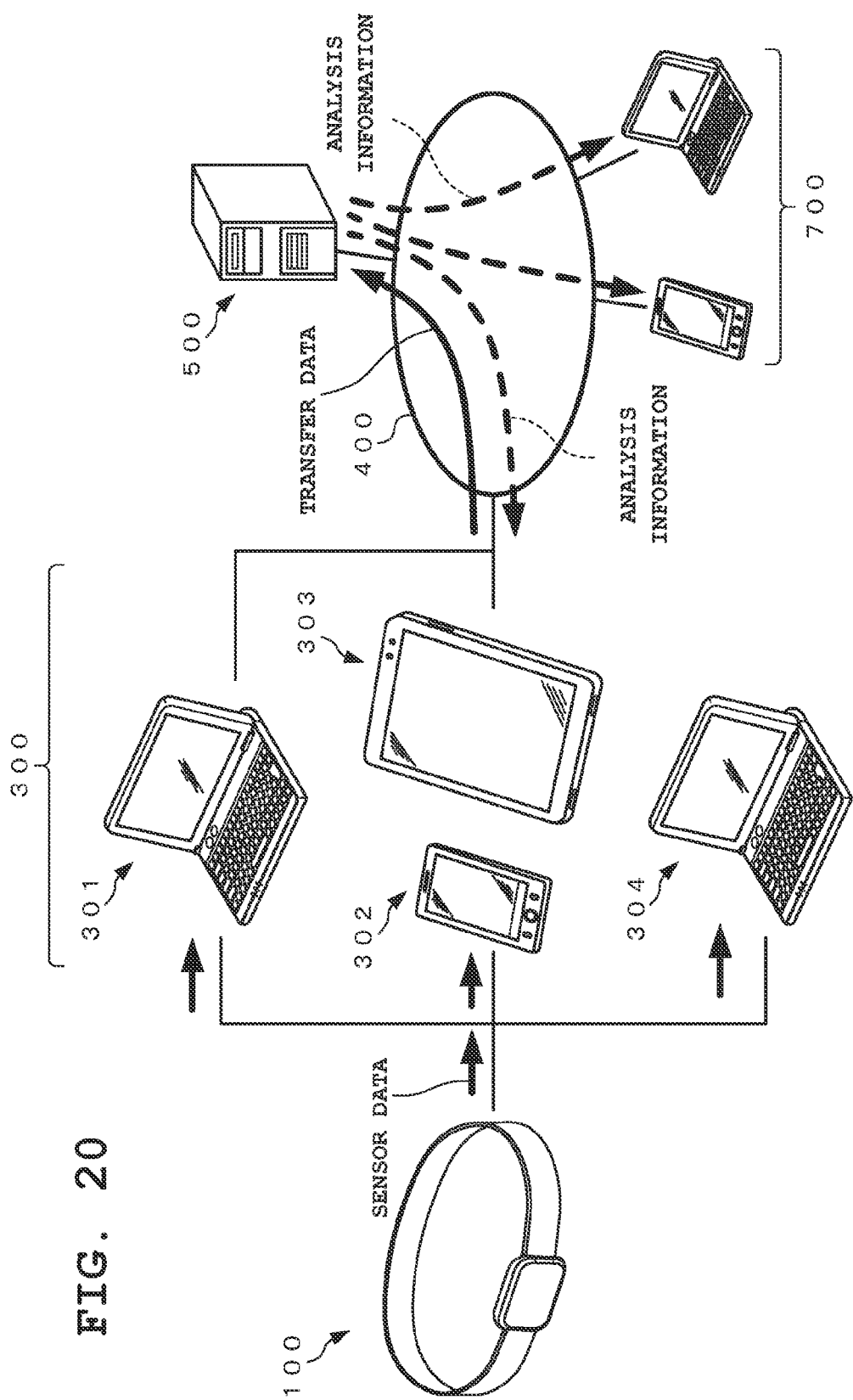
FIG. 20 is a conceptual diagram of an exercise support device according to a fourth embodiment of the present invention.

FIG. 20 is a conceptual diagram of the exercise support device according to the fourth embodiment of the present invention.

Figure 21:
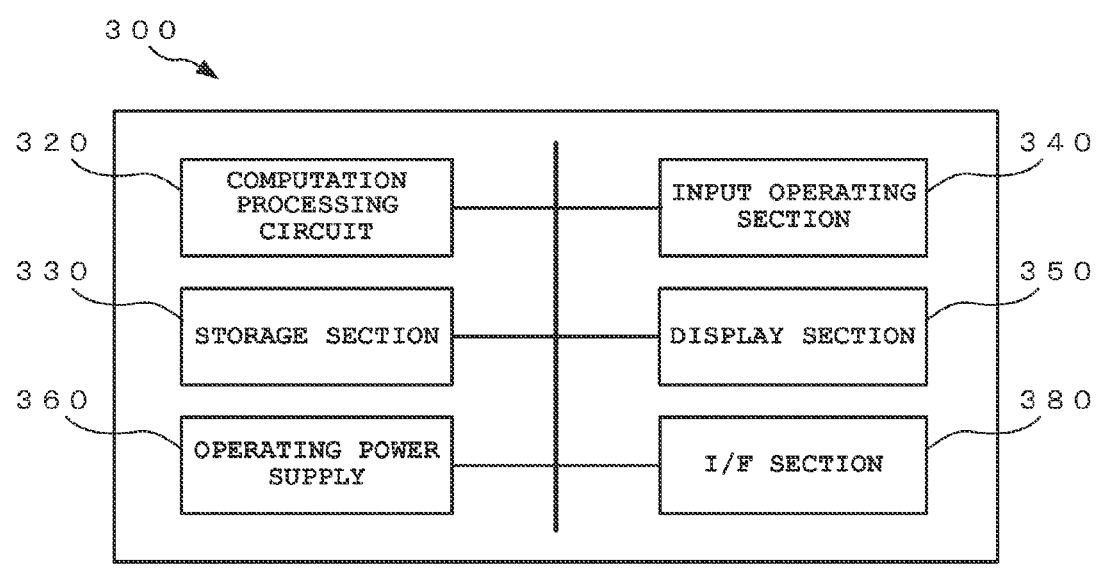
FIG. 21 is a functional block diagram showing a structural example of an information processing device to be applied to the exercise support device according to the fourth embodiment.
Figure 22:
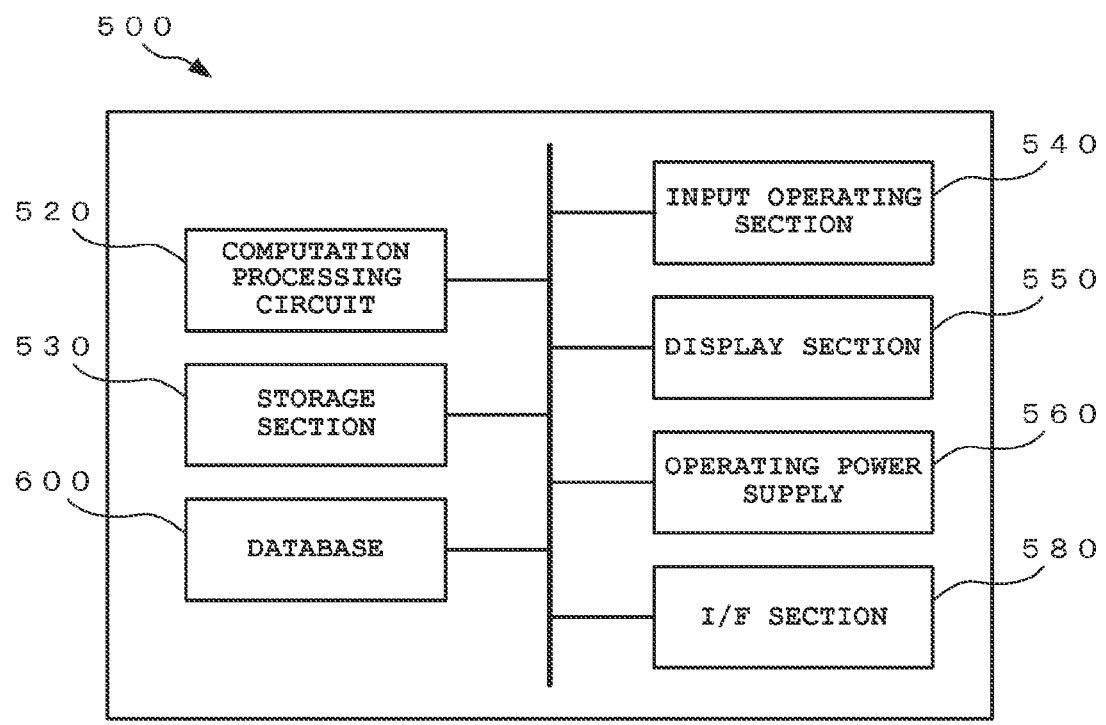
FIG. 22 is a functional block diagram showing a structural example of a network server to be applied to the exercise support device according to the fourth embodiment.

FIG. 21 is a functional block diagram showing a structural example of an information processing device to be applied to the exercise support device according to the present embodiment, FIG. 22 is a functional block diagram showing a structural example of a network server to be applied to the exercise support device according to the present embodiment.

Here, sections equivalent to those of the above-described first to third embodiments are provided with the same or equivalent reference numerals, and descriptions therefor are simplified.

The exercise support device according to the fourth embodiment includes, for example, the chest device 100, an information processing device 300, a network 400, a network server 500, and a user terminal 700, as shown in FIG. 20.

Here, the chest device 100 has the same structure as that of the third embodiment except that it has a function for storing sensor data obtained while exercising in the storage section 130 as needed and a function for transferring data to and from the information processing device 300 outside the chest device 100.

That is, the chest device 100 does not have the function described in the above-described first to third embodiments which is required for estimating a foot landing period of the user US based on sensor data obtained while exercising, analyzing the change, abnormality, and the like of the foot landing period and various exercise information, and generating a notification signal according to the judgment results.

The information processing device 300 is an electronic device capable of transferring various data to and from at least the chest device 100 by the above-described wireless or wired communication method or via a storage medium such as a memory card.

This information processing device 300 has a function for connecting to the network 400 and a web browser function as described below.

As the information processing device 300, for example, a general-purpose device such as a notebook-type or desktop-type personal computer 301, a smartphone 302, or a tablet terminal 303, or a dedicated device as an exercise support device (omitted in the drawing) is adopted as shown in FIG. 20.

In the present embodiment, the information processing device 300 can be applied as the user terminal 700 described below.

Specifically, the information processing device 300 mainly includes, for example, a computation processing circuit 320, a storage section 330, an input operating section 340, a display section 350, an operating power supply 360, and an I/F section 380, as shown in FIG. 21.

The computation processing circuit 320 is a computation processing device such as a CPU or MPU including a timing function and, by performing processing in accordance with a predetermined control program, controls an operation in each section, such as an operation of displaying various information on the display section 350 and a data transfer operation in the interface section 380.

The storage section 330 temporarily stores sensor data (at least an acceleration signal) transferred from the chest device 100 in a predetermined storage area.

In a configuration where the information processing device 300 is adopted as the user terminal 700 for viewing a foot landing period of the user US calculated in the network server 500 and judgment results of the foot landing period and various exercise information acquired by analysis processing, the storage section 330 stores analysis information received via the network 400 in a predetermined storage area.

Note that the storage section 330 may be partially or entirely a removable storage medium so as to be removable from the information processing device 300, as in the case of the above-described chest device 100 and wrist device 200.

The input operating section 340 is an input device such as a keyboard, a mouse, a touchpad, or a touch panel provided to the personal computer 301, the smartphone 302, the tablet terminal 303, or the like.

This input operating section 340 is used to select an icon or a menu displayed on the display section 350 or to indicate a point on a screen display, whereby a function corresponding to the icon, the menu, or the point is performed.

The display section 350 has a display panel of, for example, a liquid-crystal-type or a light-emitting-element-type, and displays a communication status or a transfer status when at least the above-described sensor data received from the chest device 100 is transferred to the network server 500 via the network 400 described below.

In the configuration where the information processing device 300 is adopted as the user terminal 700, the display section (information providing section) 350 displays the above-described sensor data, a foot landing period, various exercise information, their analysis data, and judgment results as numerical value data, graphs, or the like.

The operating power supply 360 supplies driving electric power to each section of the information processing device 300.

In a portable electronic device (mobile device) such as the smartphone 302 or the tablet terminal 303, a secondary battery such as a lithium-ion battery is adopted as the operating power supply 360.

In the notebook-type personal computer 301 or the like, a secondary battery or a commercial power supply is applied.

In a desktop-type personal computer, a commercial power supply is applied.

The interface section 380 functions as an interface when sensor data transmitted from the chest device 100 is received.

The interface section 380 has a function for connecting to the network 400 such as the Internet or a LAN (Local Area Network), and functions as an interface when sensor data (represented as "transfer data" in the drawing) and analysis information are transmitted to and received from the network server 500.

The network 400 is a computer network where sensor data (transfer data) and analysis information can be transmitted and received between the above-described information processing device 300 and the network server 500.

Here, the network 400 may be a publicly-usable network such as the Internet, or a network that is limitedly usable by a specific group such as a business enterprise, an organization specific to an area, or an educational organization.

The network server 500 is connected to the information processing device 300 via the above-described network 400.

This network server 500 is an application server having at least a function for estimating a foot landing period of the user US, analyzing the change, abnormality, and the like of the foot landing period and various exercise information, and generating a notification signal in accordance with the judgment results, based on sensor data obtained while exercising and transferred from the information processing device 300, as described in the first to third embodiments.

Specifically, the network server 500 mainly includes, for example, a computation processing circuit 520, a storage section 530, an input operating section 540, a display section 550, an operating power supply 560, an I/F section 580, and a database 600, as shown in FIG. 22.

The input operating section 540, the display section 550, and the operating power supply 560 have functions equivalent to those of the input operating section 340, the display section 350, and the operating power supply 360 of the above-described information processing device 300, respectively, and therefore are not described herein.

The database 600 may be incorporated in the network server 500, or may be connected externally to the network server 500 or directly to the network 400.

The computation processing circuit 520 and the storage section 530 have functions equivalent to those of the computation processing circuit 120 and the storage section 130 described in the above-described first to third embodiments.

That is, the computation processing circuit 520, which is a computation processing device having a timing function, performs processing in accordance with a predetermined control program, and thereby controls an operation in each section, such as an operation of storing and reading sensor data (transfer data), analysis information, and the like in and from the storage section 530 and the database 600, an operation of displaying various information on the display section 550, and a data transfer operation in the interface section 580.

By performing processing in accordance with a predetermined algorithm program, the computation processing circuit 520 performs processing for estimating a foot landing period of the user US and analyzing the change, abnormality, and the like of the foot landing period and various exercise information, based on sensor data (transfer data) received via the interface section 580, as described in the first to third embodiments.

The analysis data and the judgment results generated in this analysis processing are stored in, for example, a predetermined storage area of the database 600.

Subsequently, by the user US operating the user terminal 700 to access the network server 500, the computation processing circuit 520 accordingly reads out the sensor data and various exercise information and their analysis data and judgment results from the database 600 in response to the request from the user US, and generates wave display data so that they are displayed by a web browser provided to the user terminal 700 in a display format using numerical values, graphs, or the like.

Then, the web display data is transmitted as analysis information to the user terminal 700 via the network 400.

The storage section 530 temporarily stores various data that are used when processing is performed in the above-described computation processing circuit 520 in accordance with a predetermined control program or algorithm program or data that are generated when processing is performed in accordance with the program.

The interface section 580 functions as an interface when sensor data transferred from the above-described information processing device 300 is received or when a foot landing period and various exercise information calculated in the network server 500, and analysis information including their analysis data and judgment results are transmitted to the user terminal 700.

The user terminal 700 is an electronic device having a structure equivalent to that of the above-described information processing device 300 (refer to FIG. 21)

By accessing the network server 500, the user terminal 700 receives, via the network 400, web display data generated in the network server 500 and displays the web display data by the web browser.

As a result, a foot landing period and various exercise information calculated based on sensor data obtained while exercising and their analysis data and judgment results are displayed on the display section in a form of numerical value data, graphs, or the like.

Note that, as the user terminal 700, the information processing device 300 used for transferring sensor data to the network server 500 may be applied as it is, or an electronic device having a network connection function different from the information processing device 300 may be applied.

(Exercise Support Method)

Next, the exercise support method for the exercise support device according to the present embodiment is described.

Figure 23:
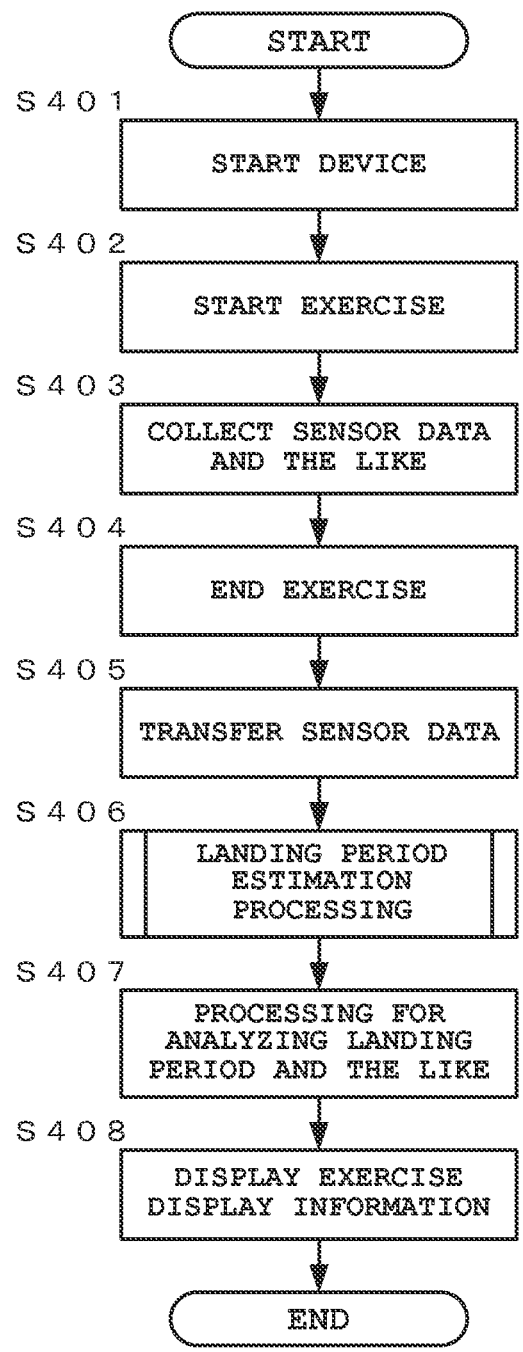
FIG. 23 is a flowchart of an example of an exercise support method to be performed for the exercise support device according to the fourth embodiment.

FIG. 23 is a flowchart of an example of the exercise support method to be performed for the exercise support device according to the present embodiment.

Here, procedures equivalent to those of the above-described first to third embodiments are simplified.

In the exercise support method according to the present embodiment, the user US first turns on the chest device 100 worn on the body to activate it (Step S401), as shown in the flowchart of FIG. 23.

Next, simultaneously with the start of the user's exercise, or before or after the start of the user's exercise, the chest device 100 starts a sensing operation (Step S402). As a result, sensor data (at least an acceleration signal) of the user US while exercising is collected and stored in a predetermined storage area of the storage section 130 (Step S403).

This collection of sensor data continues until the user US ends the sensing operation in the chest device 100 simultaneously with the end of the exercise or before or after the end of the exercise (Step S404).

Then, after the end of the user's exercise, the sensor data stored in the storage section 130 of the chest device 100 is transferred to the information processing device 300 by a wireless communication method or a wired communication method or via a memory card or the like, and further transferred by the information processing device 300 to the network server 500 via the network 400 (Step S405).

The sensor data (transfer data) transferred to the network server 500 is stored in a predetermined storage area of the storage section 530 or the database 600.

Next, in the network server 500, the computation processing circuit 520 performs processing for estimating a foot landing period of the user US, analyzing the change, abnormality, and the like of the foot landing period and various exercise information, and generating a notification signal in accordance with the judgment results, based on the sensor data stored in the storage section 530, as with the above-described first to third embodiments (Steps S406 and S407).

The calculated foot landing period and various exercise information, and their analysis data and judgment results are stored in a predetermined storage area of the database 600.

Next, the user US operates the information processing device 300 or the user terminal 700 to access the network server 500 via the network 400 so as to perform an operation for requesting the display of arbitrary analysis information.

As a result, in the network server 500, the computation processing circuit 520 reads out the foot landing period, various exercise information, and their analysis data and judgment results stored in the database 600, and generates web display data of a predetermined display format in accordance with the request.

The generated web display data is transmitted as analysis information from the interface section 580 to the information processing device 300 or the user terminal 700 via the network 400.

Then, the analysis information transmitted to the information processing device 300 or the user terminal 700 is displayed on the display section 350 by a web browser in a form of numerical value data, graphs, or the like (Step S408).

As described above, in the present embodiment, the chest device 100 worn on the chest of the user US collects sensor data while exercising, and the collected sensor data is transferred to the network server 500 by the information processing device 300 via the network 400 after the end of the exercise.

Then, the network server 500 calculates a foot landing period of the user US as described above and analyzes the change, abnormality, and the like of the foot landing period and various exercise information.

Then, by the user US operating the information processing device 300 or the user terminal 700 to access the network server 500, the sensor data, the foot landing period, the various exercise information, their analysis data and judgment result, and the like are transmitted as analysis information from the network server 500, and displayed on the display section 350 of the information processing device 300 or the user terminal 700.

As a result of this configuration, in the present embodiment, only by wearing the exercise support device (chest device 100) having a simple structure, the user US can intuitively and visually grasp the change, abnormality, and the like of a foot landing period and various exercise information, and therefore can effectively reflect them in future exercises.

Also, in the present embodiment, the chest device 100 is only required to have a function for collecting and storing sensor data while exercising, and the information processing device 300 is only required to have a function for transferring sensor data to the network server 500 and a function for displaying analysis information by a web browser.

Therefore, the exercise support device according to the present embodiment can be structured easily and inexpensively.

Moreover, in the present embodiment, the network server 500 calculates a foot landing period of the user US and analyzes change tendencies of the foot landing period and various exercise information.

As a result of this configuration, by an algorithm program regarding the calculation of a foot landing period and an algorithm program regarding the analysis of a foot landing period and various exercise information being updated as needed in the network server 500, latest methods can be always performed for the calculation processing and the analysis processing, whereby the user US can precisely grasp his or her own exercise status.

In the present embodiment, sensor data (at least an acceleration signal) obtained by the chest device 100 is transferred by the information processing device 300 to the network server 500 via the network 400 and the network server 500 calculates a foot landing period of the user US as described above and analyses the change, abnormality, and the like of the foot landing period and various exercise information. However, the present invention is not limited thereto.

As shown in FIG. 20, a configuration may be adopted in which the information processing device 300 provided outside the chest device 100 (for example, the notebook-type or desktop-type personal computer 304) calculates a foot landing period as described above and analyze the foot landing period and various exercise information.

In this configuration, the information processing device 300 has a function for calculating a foot landing period and analyzing the foot landing period, various exercise information, and the like by performing processing according to a predetermined algorithm program in the computation processing circuit 320 shown in FIG. 21, and is not required to have a function for connecting to the network 400.

As a result of this configuration, even when the information processing device 300 is in an environment where connection to the network 400 is impossible (or difficult), the processing for calculating a foot landing period and the processing for analyzing the foot landing period and various exercise information can be favorably performed, and the analysis data and judgment results of the foot landing period and the various exercise information can be displayed on the display section 350 as numerical value data, graphs, or the like.

Accordingly, change tendencies of the foot landing period and the various exercise information can be visually provided to the user US, whereby the user US can intuitively grasp his or her own exercise status and effectively reflect them in future exercises.

Also, in each of the above-described embodiments, the chest device 100 including the acceleration measuring section 110 and the angular velocity measuring section 170 is worn on the chest. However, the present invention is not limited thereto.

The present invention may be any type of device as long as it can obtain at least acceleration signals in three axis direction while exercising (running). In addition, it may be worn on another part of the body, such as the upper body including the hip or neck, or, more preferably, the body trunk except the four limbs. According to verification by the inventor, by the present invention being worn on the body trunk, a foot landing period can be accurately calculated (estimated) with the methods according to the above-described embodiments.

Moreover, in each of the above-described embodiments, running exercise has been exemplarily described as an exercise to which the present invention is applied. However, the present invention is not limited thereto. For example, the present invention may be applied to various exercises where cyclic motions such as walking are performed.

While the present invention has been described with reference to the preferred embodiments, it is intended that the invention be not limited by any of the details of the description therein but includes all the embodiments which fall within the scope of the appended claims.

What is claimed is:
1. An exercise support device comprising:
   an acceleration sensor which obtains acceleration signals in three axis directions including a vertical direction, a longitudinal direction, and a lateral direction corresponding to a motion of a body of a user performing an exercise with cyclically moving feet; and
   an information providing device which provides the user with exercise support information;
   a processor which is configured to:
   obtain a first maximum value within a period of one cycle of a foot movement of the user in an acceleration signal in the vertical direction obtained by the acceleration sensor,
   search for a first change point related to foot landing and takeoff motions of the user in a composite acceleration signal obtained by combining acceleration signals in at least two of the three axis directions, in a forward direction of a time point of a second maximum value of the composite acceleration signal, and search for a second change point related to foot landing and takeoff motions of the user in the composite acceleration signal, in a backward direction of the time point of the second maximum value, within the period of one cycle, obtain a period of time between the first change point and the second change point as a change point interval, when the first change point and the second change point are detected by the searching, and calculate a foot landing period of the user while exercising based on the first maximum value of the acceleration signal in the vertical direction obtained by the acceleration accelerated sensor and the change point interval obtained by the processor, judge quality of the calculated foot landing period based on a reference value and a reference range for the foot landing period, and provide, by the information providing device, the user with exercise support information based on a judgment result.

2. The exercise support device according to claim 1, wherein the processor calculates the foot landing period by an equation $T=a \times P + b \times W + c \times P \times W$ where the foot landing period is T, the first maximum value is P, the change point interval is W, a and b are positive constants, and c is a negative constant.

3. The exercise support device according to claim 1, wherein the processor calculates the foot landing period based on the first maximum value of the acceleration signal in the vertical direction, when at least one of the first change point and the second change point is not detected.

4. The exercise support device according to claim 3, wherein the processor calculates the foot landing period by an equation of foot landing period $T = d \times (1/P)$ where the foot landing period is T, the first maximum value is P, and d is a positive constant.

5. The exercise support device according to claim 1, wherein the acceleration signals in the two axis directions for generating the composite acceleration signal are the acceleration signal in the vertical direction and an acceleration signal in the longitudinal direction.

6. The exercise support device according to claim 1, wherein the processor:

searches for a minimum value equal to or smaller than a predetermined threshold value in the forward direction and the backward direction of the time point of the second maximum value of the composite acceleration signal, obtains, when at least one minimum value is found in each of the forward direction and the backward direction of the time point of the second maximum value, a first minimum value of found minimum values which is positioned closest to time progress to the second maximum value in the forward direction of the second maximum value as the first change point, and a second minimum value which is positioned closest to time progress to the second maximum value in the backward direction of the second maximum value as the second change point, and obtains a period of time between the first minimum value and the second minimum value as the change point interval.

7. The exercise support device according to claim 1, wherein the processor:

corrects values of the acceleration signals of each axis by rotating each axis of the acceleration signals such that the acceleration signal in the vertical direction obtained by the acceleration sensor coincides with a gravity direction, obtains the first maximum value of the acceleration signal in the vertical direction based on the corrected acceleration signals, and searches for the first change point and the second change point based on the corrected acceleration signals.

8. The exercise support device according to claim 7, further comprising:

an angular velocity sensor which obtains angular velocity signals in rotating directions of three axes of the user while exercising, wherein the processor estimates the gravity direction based on the angular velocity signals obtained by the angular velocity sensor and corrects the values of the acceleration signals.

9. The exercise support device according to claim 1, wherein the acceleration sensor, the storage device, the processor, and the information providing device are directly or indirectly connected to a network, wherein the processor obtains the first maximum value of the acceleration signal in the vertical direction, searches for the first change point and the second change point of the composite acceleration signal, and calculates the foot landing period, respectively, based on the acceleration signals received via the network, and wherein the information providing device provides the user with the exercise support information based on the notification signal in accordance with at least a result received via the network.

10. The exercise support device according to claim 1, further comprising:

a storage device which stores the acceleration signals obtained by the acceleration sensor as needed, wherein the processor obtains the first maximum value of the acceleration signal in the vertical direction, searches for the first change point and the second change point, and calculates the foot landing period, respectively, based on the acceleration signals stored in the storage device after end of the exercise.

11. A control method for controlling an exercise support device, the method comprising:

a step of obtaining, by an acceleration sensor, acceleration signals in three axis directions including a vertical direction, a longitudinal direction, and a lateral direction corresponding to a motion of a body of a user performing exercise with cyclically moving feet;

a step of obtaining, by a processor, a first maximum value within a period of one cycle of a foot movement of the user in an acceleration signal in the vertical direction obtained by the acceleration sensor;

a step of searching, by the processor, for a first change point related to foot landing and takeoff motions of the user in a composite acceleration signal obtained by combining acceleration signals in at least two of the three axis directions, in a forward direction of a time point of a second maximum value of the composite acceleration signal, and searching for a second change point related to foot landing and takeoff motions of the user in the composite acceleration signal, in a backward direction of the time point of the second maximum value, within the period of one cycle;

a step of obtaining, by the processor, a period of time between the first change point and the second change point as a change point interval, when the first change point and the second change point are detected in the step of searching for the first change point and the second change point, and calculating a foot landing period of the user while exercising based on the first maximum value of the acceleration signal in the vertical direction obtained by the acceleration sensor and the change point interval obtained by the processor;

a step of judging quality of the calculated foot landing period based on a reference value and a reference range for the foot landing period; and a step of providing, by an information providing device, the user with exercise support information based on a judgment result.

12. The control method according to claim 11, wherein the foot landing period in the step of calculating the foot landing period is calculated by an equation $T=a\times P+b\times W+c\times P\times W$ where the foot landing period is T, the first maximum value is P, the change point interval is W, a and b are positive constants, and c is a negative constant.

13. The control method according to claim 11, further comprising:

a step of calculating the foot landing period based on the first maximum value of the acceleration signal in the vertical direction, when at least one of the first change point and the second change point is not detected in the step of searching for the first change point and the second change point.

14. The control method according to claim 13, wherein the foot landing period in the step of calculating the foot landing period is calculated by an equation of foot landing period $T=d\times(1/P)$ where the foot landing period is T, the first maximum value is P, and d is a positive constant.

15. The control method according to claim 11, wherein the step of searching for the first change point and the second change point includes a step of searching for a minimum value equal to or smaller than a predetermined threshold value in the forward direction and the backward direction of the time point of the second maximum value of the composite acceleration signal, and a step of obtaining, when at least one minimum value is found in each of the forward direction and the backward direction of the time point of the second maximum value, a first minimum value of found minimum values which is positioned closest to time progress to the second maximum value in the forward direction of the second maximum value as the first change point, and a second minimum value which is positioned closest to time progress to the second maximum value in the backward direction of the second maximum value as the second change point, and wherein the step of calculating the foot landing period includes a step of obtaining a period of time between the first minimum value and the second minimum value as the change point interval.

16. A non-transitory computer-readable medium having stored thereon a control program for controlling an exercise support device that is executable by a computer, the control program being executable by the computer to perform functions comprising:

processing for obtaining, by an acceleration sensor, acceleration signals in three axis directions including a vertical direction, a longitudinal direction, and a lateral direction corresponding to a motion of a body of a user performing exercise with cyclically moving feet;

processing for obtaining a first maximum value within a period of one cycle of a foot movement of the user in an acceleration signal in the vertical direction obtained by the acceleration sensor;

processing for searching for a first change point related to foot landing and takeoff motions of the user in a composite acceleration signal obtained by combining acceleration signals in at least two of the three axis directions, in a forward direction of a time point of a second maximum value of the composite acceleration signal, and a second change point related to foot landing and takeoff motions of the user in the composite acceleration signal, in a backward direction of the time point of the second maximum value, within the period of one cycle;

processing for obtaining a period of time between the first change point and the second change point as a change point interval, when the first change point and the second change point are detected in the processing for searching for the first change point and the second change point, and calculating a foot landing period of the user while exercising based on the first maximum value of the acceleration signal in the vertical direction obtained by the acceleration sensor and the change point interval;

processing for judging quality of the calculated foot landing period based on a reference value and a reference range for the foot landing period; and processing for providing, by an information providing device, the user with exercise support information based on a judgment result.

17. The non-transitory computer-readable storage medium according to claim 16, wherein the foot landing period is calculated based on the first maximum value of the acceleration signal in the vertical direction, when at least one of the first change point and the second change point is not detected in the processing for searching for the first change point and the second change point.

* * * * *